US012626793B2

(12) United States Patent (10) Patent No.: US 12,626,793 B2
Dressler et al. (45) Date of Patent: May 12, 2026

(54) BUSINESS TO CUSTOMER COMMUNICATION PORTAL

(71) Applicant: Rhinogram Inc., Chattanooga, TN (US)

(72) Inventors: Keith Dressler, Ooltewah, TN (US); Bo Ferger, Lakesite, TN (US); Douglas Ford, Signal Mountain, TN (US); Rob Whelan, Daniel Island, SC (US); Yasser Ansari, New York, NY (US); Yanis Markin, Moscow (RU)

(73) Assignee: Rhinogram Inc., Chattanooga, TN (US)

( * ) Notice: Subject to any disclaimer, the term of this patent is extended or adjusted under 35 U.S.C. 154(b) by 0 days.

(21) Appl. No.: 18/136,136

(22) Filed: Apr. 18, 2023

(65) Prior Publication Data

US 2023/0298714 A1 Sep. 21, 2023

Related U.S. Application Data

(63) Continuation of application No. 15/410,431, filed on Jan. 19, 2017, now Pat. No. 11,715,550.

(Continued)

(51) Int. Cl.
G16H 10/60 (2018.01)
G06Q 10/10 (2023.01)
(Continued)

(52) U.S. Cl.
CPC ............. *G16H 10/60* (2018.01); *G06Q 10/10* (2013.01); *G06Q 10/1093* (2013.01);
(Continued)

(58) Field of Classification Search
CPC ........ G16H 10/60; G16H 80/00; G06Q 10/10; G06Q 10/1095; G06Q 10/107;
(Continued)

(56) References Cited

U.S. PATENT DOCUMENTS 9,177,297 B2 11/2015 Thompson et al.
2001/0037219 A1 11/2001 Malik
(Continued)

FOREIGN PATENT DOCUMENTS

WO WO-2008133842 A1 * 11/2008 ............. G16H 10/60
WO WO-2010124775 A1 * 11/2010 ............... G06F 8/64
WO WO-2013134639 A2 * 9/2013 ........... H04L 51/216

*Primary Examiner* — Jason B Dunham
*Assistant Examiner* — Kimberly A. Sass
(74) *Attorney, Agent, or Firm* — Miller & Martin PLLC

(57) ABSTRACT

A multi-format communications system provides a way for a company to control information, some of which may be confidential information, such as PHI, exchanged with existing and potential customers, through individuals associated with the company in a manner preferred by the customers, particularly for non-confidential information, while maintaining a permanent record of communications. With the company maintaining control, if an employee leaves, the employee can be blocked from access to customer information, including communications. Additionally, a time-line view of all events related to a customer can be displayed including communications.

23 Claims, 22 Drawing Sheets

Related U.S. Application Data

(60) Provisional application No. 62/281,506, filed on Jan. 21, 2016.

(51) Int. Cl.
| | |
|---|---|
| *G06Q 10/1093* | (2023.01) |
| *H04L 9/40* | (2022.01) |
| *H04L 51/04* | (2022.01) |
| *H04W 4/14* | (2009.01) |

(52) U.S. Cl.
CPC .......... *H04L 51/04* (2013.01); *H04L 63/0428* (2013.01); *H04W 4/14* (2013.01)

(58) Field of Classification Search
CPC ... H04L 51/04; H04L 63/0428; H04L 51/214; H04L 51/216; H04L 63/104; H04W 4/14
USPC ............................................................ 705/3
See application file for complete search history.

(56)     References Cited

U.S. PATENT DOCUMENTS

| | | | | |
|---|---|---|---|---|
| 2002/0062367 | A1 | 5/2002 | Debber et al. | |
| 2011/0246231 | A1 | 10/2011 | Sie et al. | |
| 2012/0054716 | A1 | 3/2012 | Tailliez et al. | |
| 2012/0110343 | A1 | 5/2012 | Bandic et al. | |
| 2012/0296668 | A1* | 11/2012 | Meagher ................ | G16H 10/60 |
| | | | | 705/2 |
| 2013/0275151 | A1* | 10/2013 | Moore ................... | G16H 40/63 |
| | | | | 705/3 |
| 2013/0317753 | A1 | 11/2013 | Kamen et al. | |
| 2014/0351357 | A1 | 11/2014 | Brabec et al. | |
| 2015/0112717 | A1 | 4/2015 | Saleh et al. | |
| 2015/0205939 | A1 | 7/2015 | Sathaye et al. | |
| 2016/0147951 | A1* | 5/2016 | Francois ................ | G16H 10/65 |
| | | | | 705/3 |
| 2016/0350157 | A1 | 12/2016 | Necas | |

* cited by examiner

FIG. 7

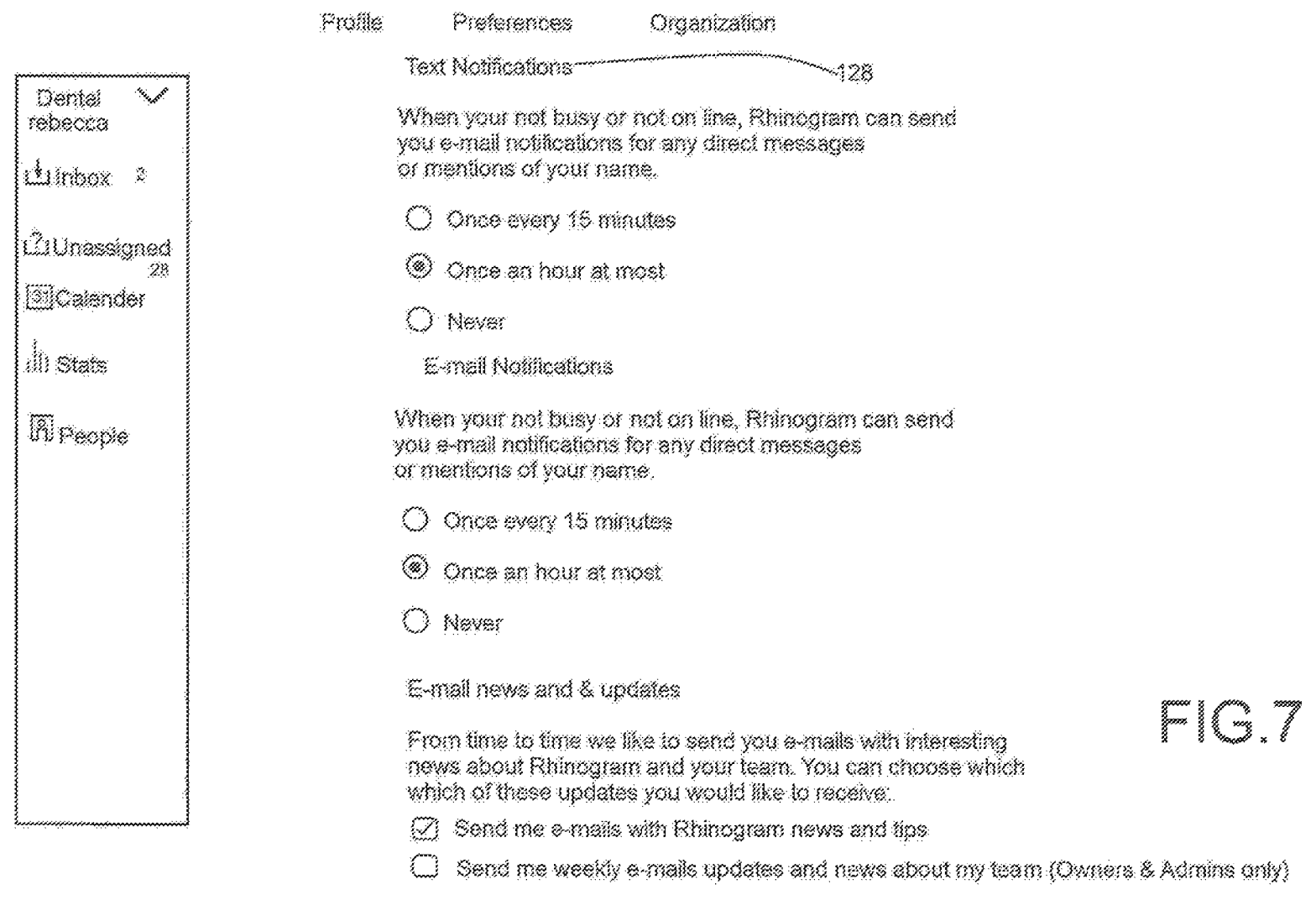

Profile    Preferences    Organization

Text Notifications ————— 128

When your not busy or not on line, Rhinogram can send you e-mail notifications for any direct messages or mentions of your name.

○ Once every 15 minutes

◉ Once an hour at most

○ Never

E-mail Notifications

When your not busy or not on line, Rhinogram can send you e-mail notifications for any direct messages or mentions of your name.

○ Once every 15 minutes

◉ Once an hour at most

○ Never

E-mail news and & updates

From time to time we like to send you e-mails with interesting news about Rhinogram and your team. You can choose which of these updates you would like to receive.

☑ Send me e-mails with Rhinogram news and tips

☐ Send me weekly e-mails updates and news about my team (Owners & Admins only)

Dental
rebecca    ∨

⤶ Inbox    9

☐ Unassigned    28
☐ Calender
�ıllı Stats
Ⓜ People

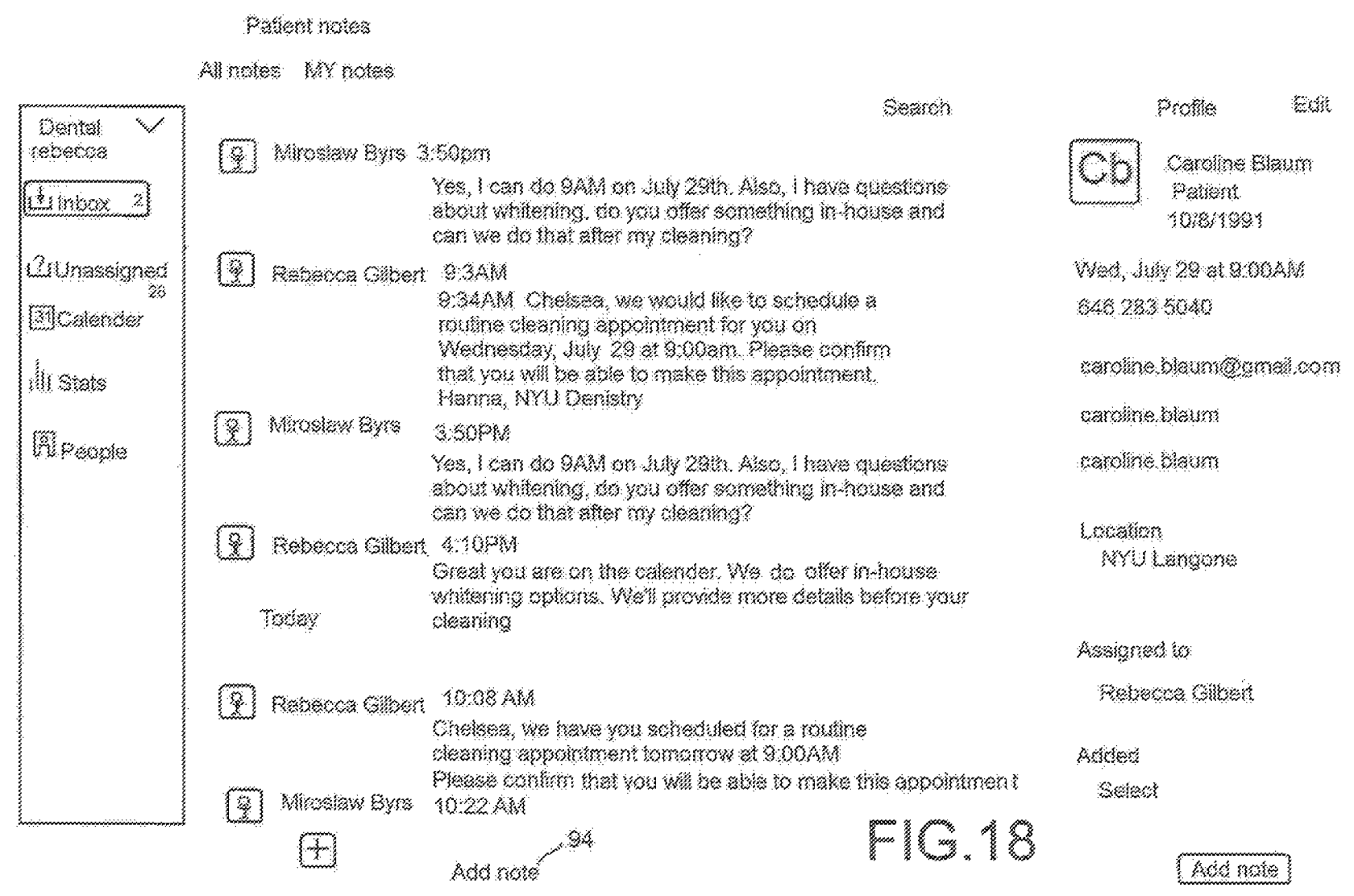

Patient notes

All notes    MY notes

Search

Profile    Edit

CB    Caroline Blaum
Patient
10/8/1991

Miroslaw Byrs 3:50pm

Yes, I can do 9AM on July 29th. Also, I have questions about whitening, do you offer something in-house and can we do that after my cleaning?

Wed, July 29 at 9:00AM 646 283 5040 caroline.blaum@gmail.com

Rebecca Gilbert    9:3AM

9:34AM Chelsea, we would like to schedule a routine cleaning appointment for you on Wednesday, July 29 at 9:00am. Please confirm that you will be able to make this appointment. Hanra, NYU Dentistry caroline.blaum caroline.blaum Location
NYU Langone Miroslaw Byrs    3:50PM Yes, I can do 9AM on July 29th. Also, I have questions about whitening, do you offer something in-house and can we do that after my cleaning?

Rebecca Gilbert    4:10PM

Great you are on the calender. We do offer in-house whitening options. We'll provide more details before your cleaning Assigned to
Rebecca Gilbert Today Rebecca Gilbert    10:08 AM Chelsea, we have you scheduled for a routine cleaning appointment tomorrow at 9:00AM Added
Select Add note Miroslaw Byrs    10:22 AM    Please confirm that you will be able to make this appointment Add note ⟋94

Dental
rebecca    ⌄

⌊ Inbox    2

⌊ Unassigned    20

Calender

Stats

People

FIG. 18

BUSINESS TO CUSTOMER COMMUNICATION PORTAL

CLAIM OF PRIORITY

This application is a continuation of and also claims a benefit of priority to U.S. patent application Ser. No. 15/410,431 filed Jan. 19, 2017, which in turn claims the benefit of U.S. Provisional Patent Application No. 62/281,506 filed Jan. 21, 2016, which are both hereby incorporated by reference in their entireties as if fully set forth herein.

FIELD OF THE INVENTION

The present invention relates to a business to a customer communication portal or system and more particularly to a communication portal which allows for customers to communicate with businesses in the channel of the customer's preference, while providing a system for allowing the business to receive the various communication streams from customers in an integrated manner, preferably assign responsible staff to those communications, and then have the staff respond back to the customers in through the communications channel of choice of the customer, preferably while maintaining a permanent record of communications between the business and the customer.

BACKGROUND OF THE INVENTION

Some individuals have used, integrated or unified communication systems which translate one communications protocol to another. For instance, software exists to convert facsimiles to e-mail. Other software products convert e-mails to faxes. Certain cell phone providers advertise conversion of voice mail to e-mail.

Each of these various systems allow for a user to customize the way they would prefer to receive messages.

Additionally, Slack is an application that is a self-contained messaging system which is becoming more popular for business to business use. While users can invite others to join other Slack members in groups, Slack is not set up to receive inbound communications from non-members. Slack is a group communication tool for teams to communicate with each other. All team members are invited to join team so they can communicate.

Public channels in Slack can be joined by any Slack member. Although teams can be set up in Slack, the obligation is on the users to join teams (or be invited to join teams) and there is not believed to be a way for a business to assign teams or alternatively assign responsibility for responding to communications. Additionally, all users need to be members of Slack for the application to work.

Slack allows for the sharing of documents, but probably not in a HIPPA compliant manner. Slack also allows users to edit or even delete messages after being sent.

While Slack allows the filtering messages, there is not an auto-assignment feature for assigning responsibility to respond to particular communications to particular individuals, apparently because Slack is being used mostly for internal communication among team members at a business and not with its external customers.

Accordingly, while Slack is certainly an attractive application for a team collaboration tool, there are believed to be improvements needed for businesses to be able to provide an integrated or unified communication system which provides the ability for the business to control the flow of communication to teams and assign responsibilities for customer communication, while still providing an ability to respond to customers in the formats of choice used by the customers. An additional security feature of being able to provide at least some secure communications for at least some applications (such as to be able to provide personal health information (PHI) and/or other sensitive material in a secure manner) would be desirable. Customer records could have secure and insecure communications. A practice could direct a patient to the secure access channel where by all prior communication methods (secure and non-secure) are accessible only from a secure portal.

In the context of some businesses such as dental offices, it is not unusual for patients to request the personal (not business) cell phone numbers of dental assistants so that the patients can text the dental assistants to attempt to reschedule appointments or for other communications. If appointments were the only thing that the patients texted the dental assistants about, that might be satisfactory for at least some dental practices. However, what if a patient receives an x-ray from another doctor and sends it via text to the dentist? Now, PHI is traveling on unsecured networks.

Additionally, it is possible that the patient may want to discuss some of their dental records with the dental assistants. This also could result in PHI being transmitted on unsecured networks.

Furthermore, the dental assistant may switch to another doctor and the entire communication record is lost by the dentist.

Worse yet, in other environments, it may be that if a staff member leaves they may take their contacts with them with no backup by the employer. This would be particularly harmful in the case of a salesperson leaving and taking contacts. Accordingly, there is believed to be a need for an improved business to consumer integrated communication system.

SUMMARY OF THE INVENTION

It is the present object of many embodiments of the present invention to provide an improved integrated or unified communication system for business to consumer use.

It is another object of many embodiments of the present invention to provide an improved integrated or unified communication system in which an administrator has the capability of grouping staff members according to teams and/or responsibility.

It is another object of many embodiments of the present invention to provide an improved integrated management communication systems in which new contacts may be auto-assigned based on various characteristics to not only teams but also to particular individuals designated to respond to communications provided by those individuals by the new contacts.

Once a staff individual (or group or team) is assigned to a message, those messages from that customer then appear at the inbox of the staff assigned as if the message had originally been addressed to them. If appropriate, a staff individual, group or team may be reassigned to a different staff individual, group or team.

It is another object of many embodiments of the present invention to provide an improved integrated communication system for use by businesses which provide a priority of communication responsibilities for particular customers in accordance with a protocol and maintain that protocol until changed by an administrator.

It is another object of many embodiments of the present invention to provide an integrated communication system which not only provides an administrative view of all communications to the business and/or subsets thereof, but also team views, while also potentially delegates out responsibility for communications preferably with filters in an automated manner (such as if the customer is already in the system to his/her team, or for an unassigned message, in accordance with a protocol such as first to an automated filter, i.e., if a message mentions "cost" to a "finance" team, etc. and then possibly to an administrator, if no filter action occurs, etc. A staff person may then respond back to incoming communications to specific individuals (possibly as groups or teams) and allow those staff individuals to respond back either through the application while notifying the involved business employees either directly or indirectly through the application which responds back to the customer through the communication channel of choice(s) of the customer. One office could have multiple teams.

The administrator can identify the time which a message was received from the customer and then provide flags and/or clocks to show a need to respond timely to the customer by the staff and auto assign responsibility, particularly if some staff member(s) are unavailable.

It is an object of many embodiments of the present invention to provide an integrated communication system which allows users to search their account or message strips by keyword or other characteristic.

It is another object of many embodiments of the present invention to provide data regarding customers such as various communication channels such as telephone, e-mail, Facebook, Twitter, a SMS number and/or others associated with a customer name. Various channels on file for a particular individual may be enabled while others disabled.

In addition to assigning a primary communications contact, it may be possible to add others which could be secondary parties which may be familiar with the communication stream of a particular customer. The communications with customers may also be non-erasable by parties to maintain a communication history or record for many embodiments.

In addition to being able to add new customers, it may also be possible to add new staff with the staff being able to be assignable to particular customers and/or teams.

Additionally, it may also be able to break further down into teams with teams having respective staff. Teams could relate to specific office such as one of a multi-office business. A location is a permission based association, which can have people, teams, and/or channels associated with it. It may also be that a particular staff member is in more than one team such as (a) in both a Finance and an Administration team of a company or (b) for an Atlanta office and a Tallahassee office, etc.

The term "Locations" can be used to associate people, channels, filters and teams together, while also preferably associating one calendar to one Location for many embodiments. Locations may also loosely be referring to departments or calendars within this application. Teams are groupings of people.

It may be possible that some staff members are provided with administrative rights while others are not.

It is another object of many embodiments of the present invention to provide an improved integrated communication system which allows multiple channels of communication to be utilized and/or selected from for various staff members.

It is another object of many embodiments of the present invention to provide an improved integrated communication system which allows for the automatic assignment of particular incoming traffic to be assigned to a particular staff such as based on the protocol such as based on key words, channels (i.e., might be similar to a particular individual), etc. Other filters may promote automatic assignment as well.

It is another object of many embodiments of the present invention to provide automated templates for use in responding to customers in the event of receiving a communication advising of an inability to make an appointment to automatically suggest alternative appointment times to that individual.

Automated templates may also be generated for reminders for appointments, etc. It is another object of many embodiments of the present invention to provide a calendar feature for displaying appointments generated by customers and staff for the customers to show capacity of the particular team and/or office location. This may assist in maximizing the efficiency of any particular team and/or office. Furthermore, it may be possible to generate a calendar view and/or chair occupation chart for particular patients and such business environments as dental practices and/or other practices in which chair assignment efficiency is particularly important to that particular business.

In addition to being able to communicate from a customer to the business in the particular format as desired by the individual such as through Facebook messaging, SMS messaging, e-mail and/or otherwise, those messages can be routed through the communication system of the business to then be able to respond and maintain communication files for their customers possibly with each customer having a communication record which could be a permanent record for some embodiments.

Still further embodiments have an ability to format Electronic Health Records (EHRs) as a time-line feature in what is believed to be a unique manner. Not only are formal doctor to patient communications regarding specific medical issues recorded along with test results, doctor's notes and even doctor to doctor communications about a particular patient maintained, but also communications initiated by the patient, and even less formal communications such as communications (regardless of the formats as described herein, such as in the preceding paragraph or any future developed communication system) or even non-conversation elements, such as appointment events, etc. One feature of at least some embodiments is to order entries in a timeline manner regardless of the type of entry. For instance, an appointment could be recorded as being created on May 1, 2016, for an appointment on Jun. 1, 2016. A conversation could occur on May 30, 2016 confirming the appointment and providing specific instructions (such as not to eat anything after midnight). The patient might text in later that afternoon confirming that they understand they are not to eat the night of May 31, 2016. A pre-appointment test may provide test results to the file on May 31, 2016, and then the doctor visit could occur on Jun. 1, 2016 resulting in more entries. In the timeline format one could view each of these entries chronologically as opposed to searching through various files to ascertain the timing of each event. This is particularly helpful in situations where some of this information is not permanently maintained, or even accessible, in the prior art (such as a text message which may have otherwise gone to a tech's personal cell phone number outside of the medical practice's control, or other information).

Not only is this system relevant to health care providers such as dentists, orthodontists, physical therapy clinics, medical offices, specialty clinics (such as dialysis, etc.), psychiatrist offices, counseling service providers, but also other businesses such as legal service providers, financial service providers (like stock brokers and/or others, etc.).

It is yet a further object of many embodiments of the present invention to provide tracking software to track response time to incoming messages by members of the organization relative to the time of receipt of the incoming message. A business can assign responsibility to respond to the various incoming messages and then preferably track response times in an effort to thereby increase customer service.

Accordingly, the business can control the receipt of communications or calls and how they come in such as by receiving phone messages, faxes, e-mails, SMS texts. Existing phone numbers can be used to receive SMS via number posting services. These can be directed to the applicants' software. The system administrator, if incoming messages for at least a team are not automatically assigned, can assign new communications to responsible individuals as well as copying other specific individuals on those communications. The staff members of the organization can then receive notifications from the application of a need to respond and after a predetermined time, the responsible party might even be switched to another party for at least some applications, possibly automatically such as if someone is out of the office, or if someone fails to respond in a pre-determined time frame. Furthermore, when receiving unsecured messages such as e-mails and others, it may be possible that if PHI information is to be shared or other confidential information shared, that the application itself may be used to communicate.

Confidential information may be sent via the application itself such as by sending a message through traditional unsecured sources such as Facebook messenger, texts, saying "Click here" to retrieve information which allows the user to then access the application through the secure application, secure channel and/or secure website. In this manner, financial matters, PHI or other confidential communications (even with attachments) may be exchanged between the parties which has not previously been possible with non-secure prior art systems.

Still some of these or other features may be desirable for some companies.

BRIEF DESCRIPTION OF THE DRAWINGS

The particular features and advantages of the invention as well as other objects will become apparent from the following description taken in connection with the accompanying drawings in which:

FIG. 7 is a screen shot showing notification of a first presently preferred embodiment of the present invention;

FIG. 11 is a screen shot showing first calendar of a first presently preferred embodiment of the present invention;

FIG. 14 is a screen shot showing a statistical response time analysis of a first presently preferred embodiment of the present invention;

FIG. 18 is a screen shot showing notes page of a presently preferred embodiment of the present invention;

DETAILED DESCRIPTION OF THE PREFERRED EMBODIMENTS

Figure 1:
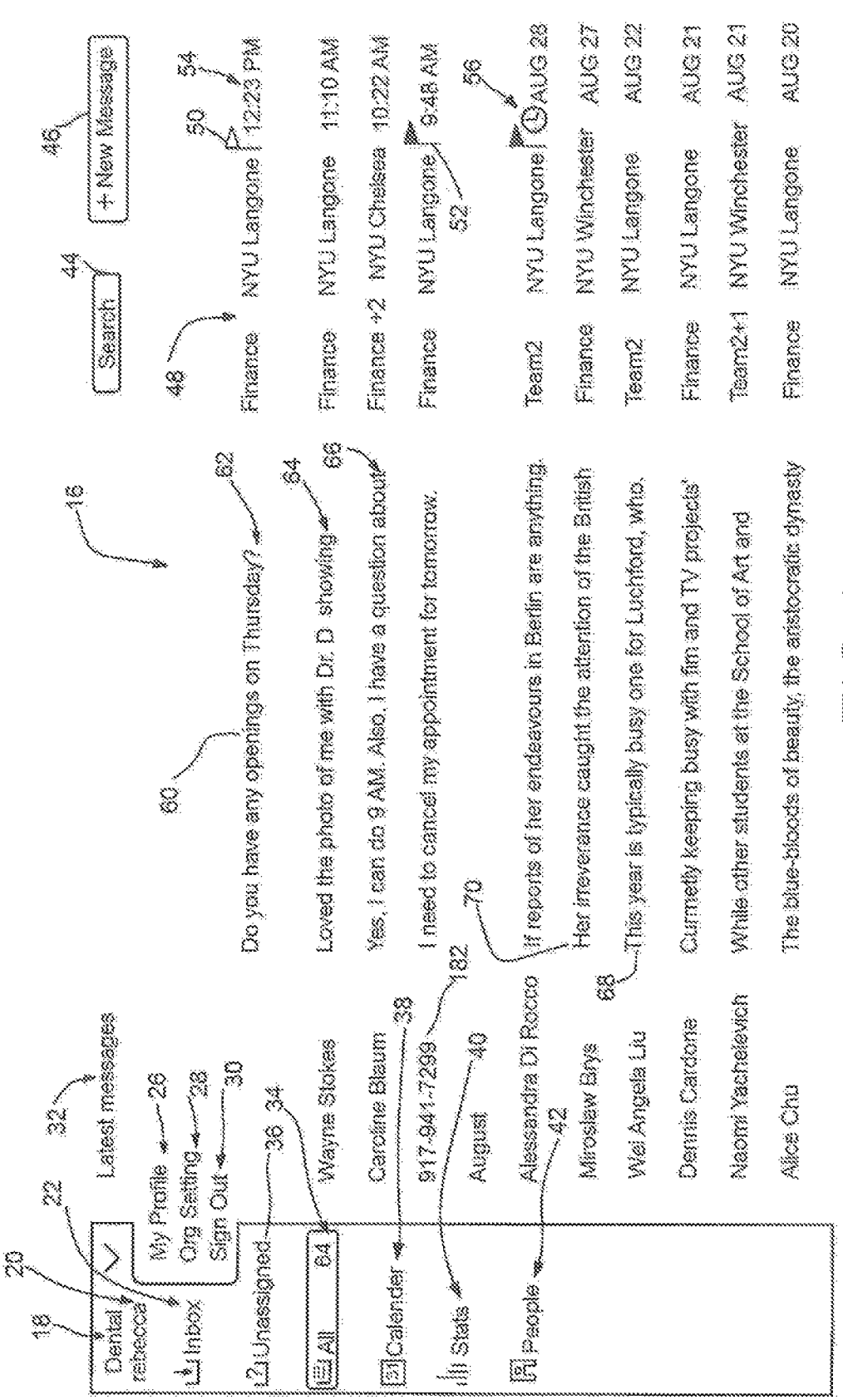
FIG. 1 is a screen shot of a first presently preferred embodiment of the present invention which shows many features.
Figure 15:
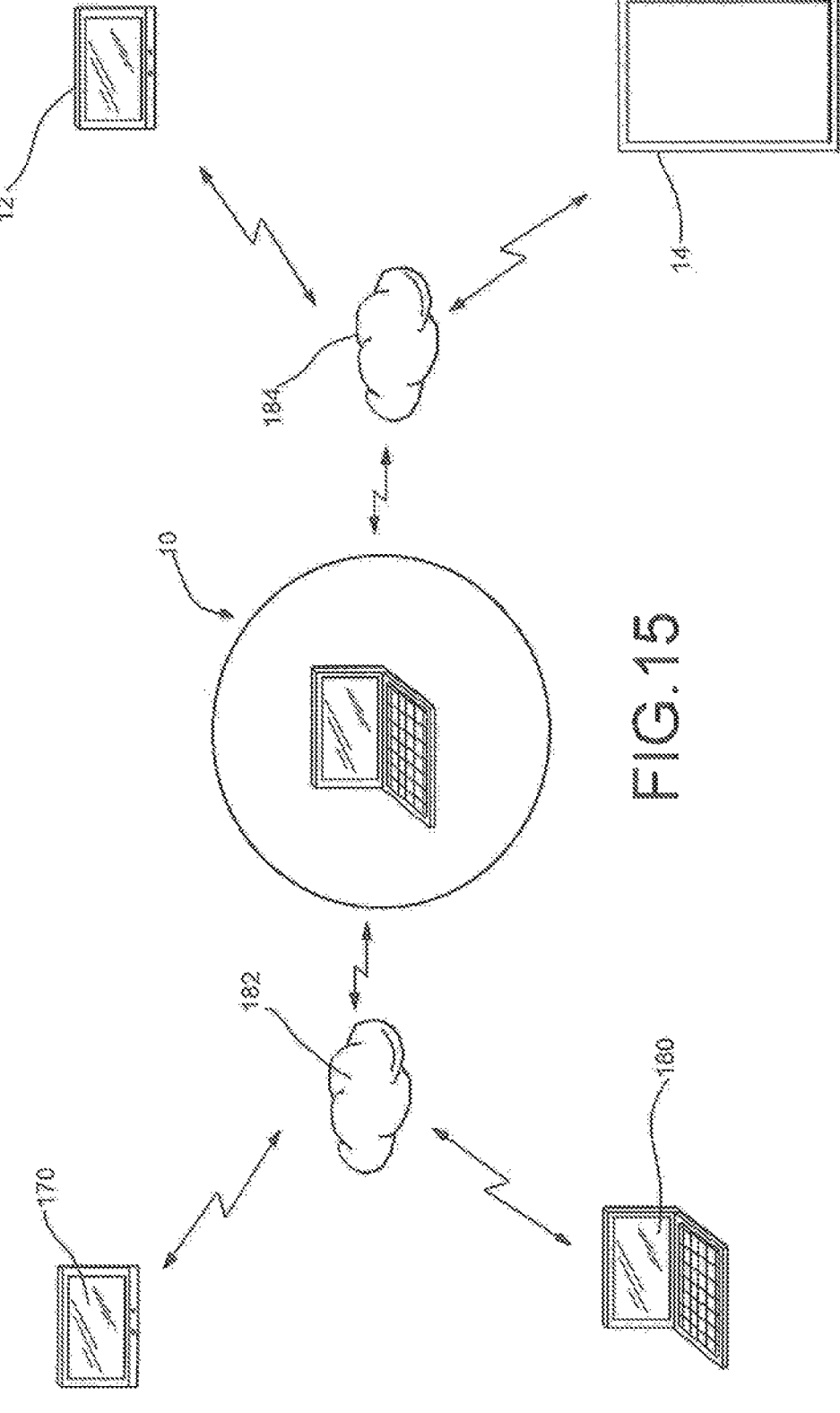
FIG. 15 is a schematic representation of the presently preferred embodiment of the present invention.

FIG. 1 shows a presently preferred embodiment of the present invention as could be displayed on a computer 10 shown in FIG. 15. Staff such as staff 12,14 and/or others as could be displayed as described in further detail below. The screen shot 16 shows a business 18 with a first staff member 20 (possibly an administrator) with an inbox 22 and drop down 24 which show "My Settings" 26, "Team Settings" 28 and possibly "Sign Out" 30. The view illustrated is an administrator view of a team of staff. Latest messages are displayed under display 32. Other selection possibilities from the screen shot 16 may include all messages 34 or other assignments 36, calendar view 38, statistical view 40 and/or people view 42. In box 32 may display the communications for which the staff member 20 is responsible.

It may also be possible to search such as using search box 44 and possibly construct new messages 46 without replying to incoming messages.

Figure 16:
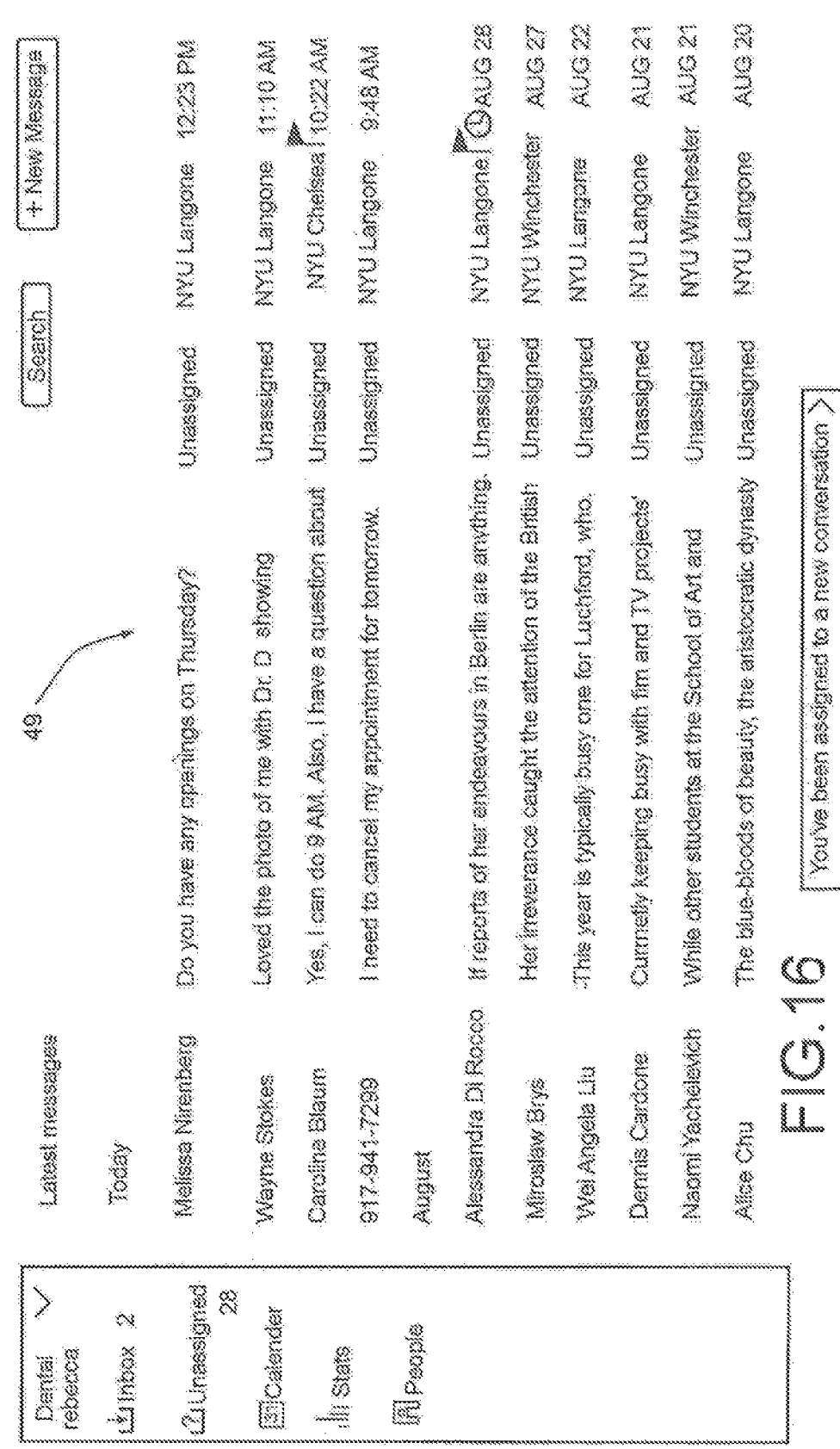
FIG. 16 is a screen shot showing an unassigned inbox of a first presently preferred embodiment of the present invention.

The first message displayed 48 as illustrated in FIG. 1 is a message assigned to the Finance team at the organization or company 18 at issue. FIG. 16 shows an unassigned message 49 which means it has not yet been assigned to a particular member of the staff. This may be an unsolicited inquiry from a potential customer asking if there are any openings on Thursday. As will be discussed below, the software of the presently preferred embodiment is scalable. Specifically, some organization or companies 18 may desire to have all not yet assigned communications be unassigned until assigned by an administrator at which time they could shift from a screen like FIG. 16 to one like FIG. 1. Other organization or companies 18 may prefer to use filters in an effort to automatically direct otherwise unassigned messages to specific individuals, teams depending on various hierarchies. For instance, all new individuals mentioning "appointment" may be assigned to a particular employee as a first priority with a second priority being that all Facebook messages be assigned to a second employee as a second priority, etc.

Referring back to FIG. 1, a first flag 50 may be displayed over first urgency and second flag 52 may be displayed for other messages showing a different urgency (such as a higher priority) as well as the time of display of time of receipt of the message 54. Clocks 56 may also be displayed for certain messages to show that after a predetermined period of time, it may be that a first responsible party 58 may be replaced with another responsibility possibly in an automatic manner by the software on the computer 10 or otherwise.

Message 60 may be displayed upon clicking and is understood that the messages may be displaying in other formats in other embodiments. Additionally, the channel of communication as represented by 62 such as an SMS message, a Facebook message 64, a Twitter message 66, an e-mail 68 or other communications possibly like communication 70 which may be through the system itself, as will be explained below which also includes the ability to transport in a secure manner as opposed to many of the other channels such as 62,64,66 and 68.

Figure 2:
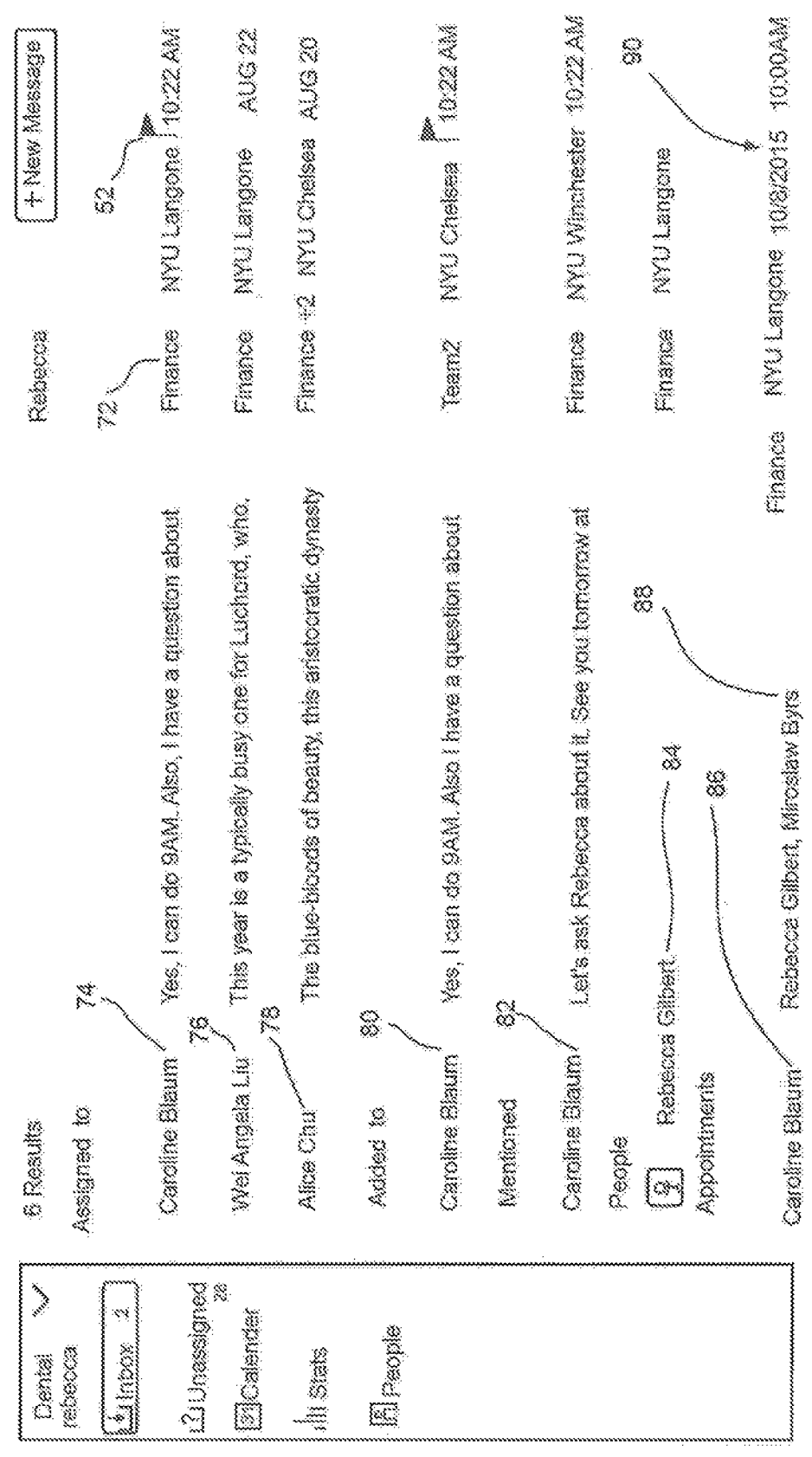
FIG. 2 is a screen shot showing a preferred embodiment showing responsibility of a single staff member of a first presently preferred embodiment of the present invention.

It may be possible to make assignments for a particular staff member such as is shown in FIG. 2 with the staff member Rebecca (provided by way of example) 72 being assigned to the three individuals 74,76,78 illustrated. Additionally, Rebecca 72 (by way of example) is "added" to a separate individual 80 and might be "mentioned" with respect to another individual 82. These added and mentioned status may affect how Rebecca 72 might be assigned to individuals 80,82 such as by auto assignment, protocol, normally or otherwise. A people portion 84 may be provided in which that staff member information is provided and/or entered. Furthermore, appointments may be provided as illustrated 86 which may show her appointment possibly with another individual 88 as well as reflecting the time and date 90 of that appointment. The screen shot of FIG. 2 can represent the "In Box" of Rebecca 72.

It may be that the flag such as flag 56 is illustrated as shown that staff member 70 has not yet responded to a particular message.

Figure 3:
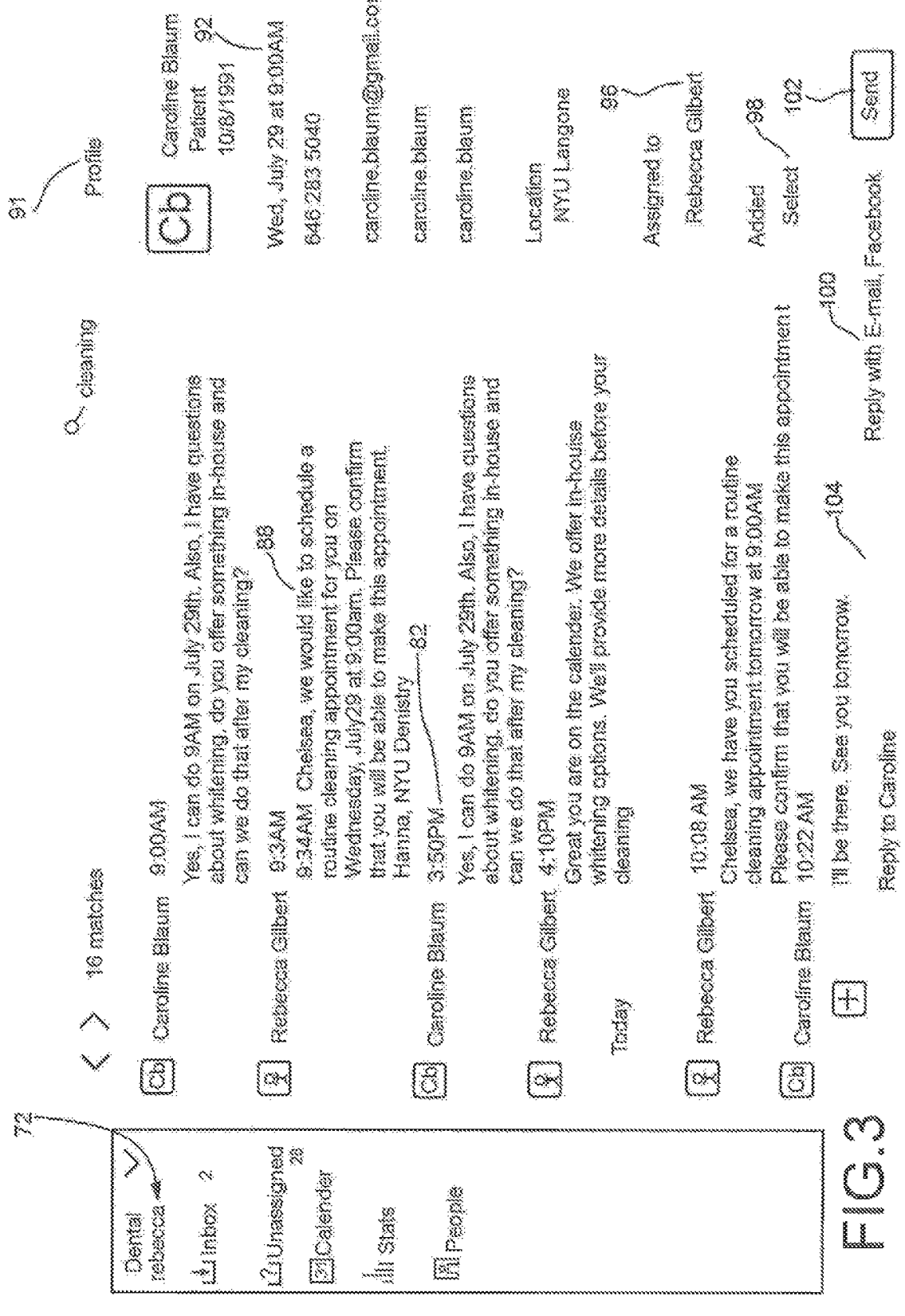
FIG. 3 is a screen shot showing a correspondence of a particular individual including a particular search term of a first presently preferred embodiment of the present invention.

FIG. 3 shows a screen shot of the communications possibly either with a search for a particular customer 82 and/or all searches for a particular word such as the word "cleaning" 88 or possibly even both. The patient of customer 82 has detail shown on the patient profile 91 which could include such information as birthdate, telephone number, SMS number, e-mail, Facebook profile, Twitter profile as well as the next appointment 92, etc. Furthermore, Notes may be provided at 94 shown in FIG. 18 or otherwise possibly in FIG. 3 and/or other figures, principal assignment (of staff member) at 96 shown in FIG. 3 as well as other "added" thereto 98. Furthermore, the preferred channels of communication can be provided at 100 as well as a send button 102 based on a reply provided at box 104.

Remember that the conversations with the particular customer 82 are intended to be provided in the form of a permanent communication record for many embodiments for each customer as well as possibly each staff member.

Figure 4:
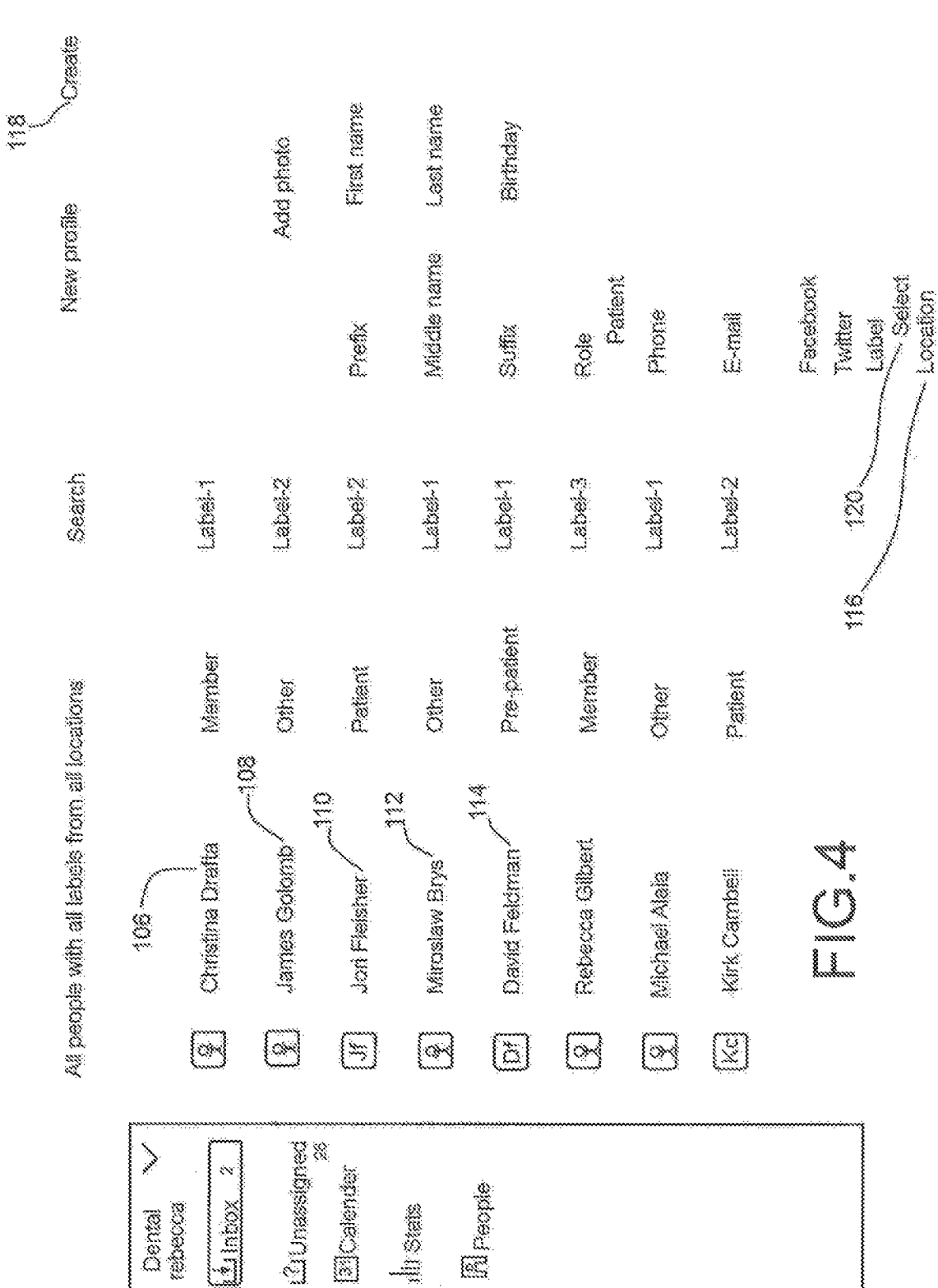
FIG. 4 is a screen shot showing people of a first presently preferred embodiment of the present invention.

FIG. 4 shows a screen shot of people which could be staff, customers or other people used within the present invention. Person 106 is shown as a member. Persons 108 and 112 are shown as others. Person 110 is shown as a patient with person 114 shown as a pre-patient. This page, for some embodiments, can allow the addition of new people into the system such as by using the create button 118 and/or edit profiles of people such as through the various data editable including labels 120 and/or location 116, and the other personal data provided.

Figure 17:
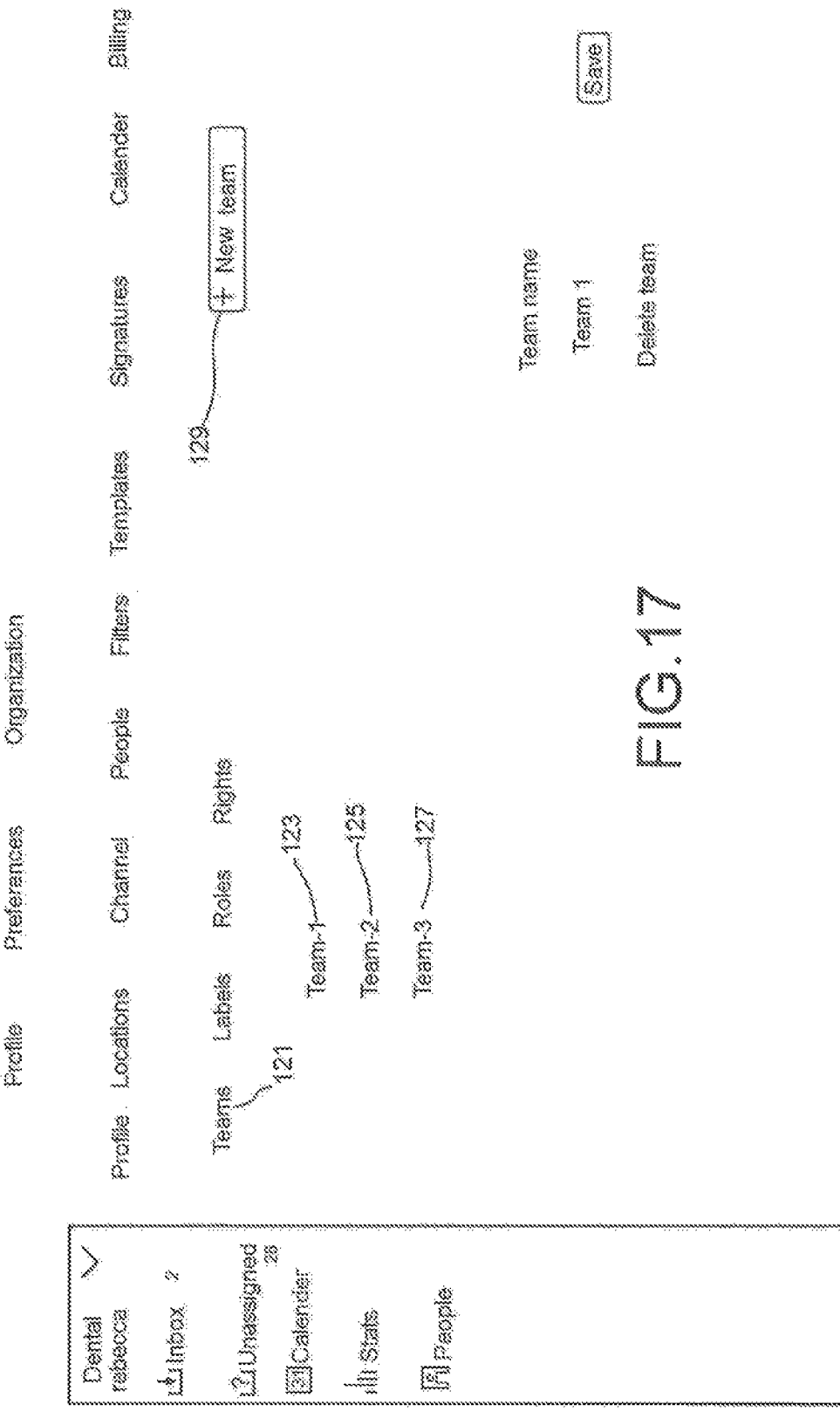
FIG. 17 is a screen shot showing of a team creation page of a first presently preferred embodiment of the present invention.

FIG. 17 provides a page to create teams and/or possibly add people to specific teams under heading teams 121 which could include specific teams 123,125,127 and/or others. People may be added to teams, departments or locations on the people page at FIG. 14 or other location. Teams could be created using button 129 or otherwise. Grouping people into teams can help manage people and simplify the task of the administrator.

For large companies and/or other companies, it may be desirable to break the company into various teams such as finance 48 illustrated in FIG. 1 or other locations or departments such as NYU Languone based on various factors. One factor of breaking a large company into various departments or locations may be that the departments could correspond to different calendars associated with an area of expertise or operation of the company or different offices (such as for a multi-office dental practice, by way of example). Accounting or operations could be departments in some companies or organizations 18. Various floors of a hospital could be departments, etc.

Figure 5:
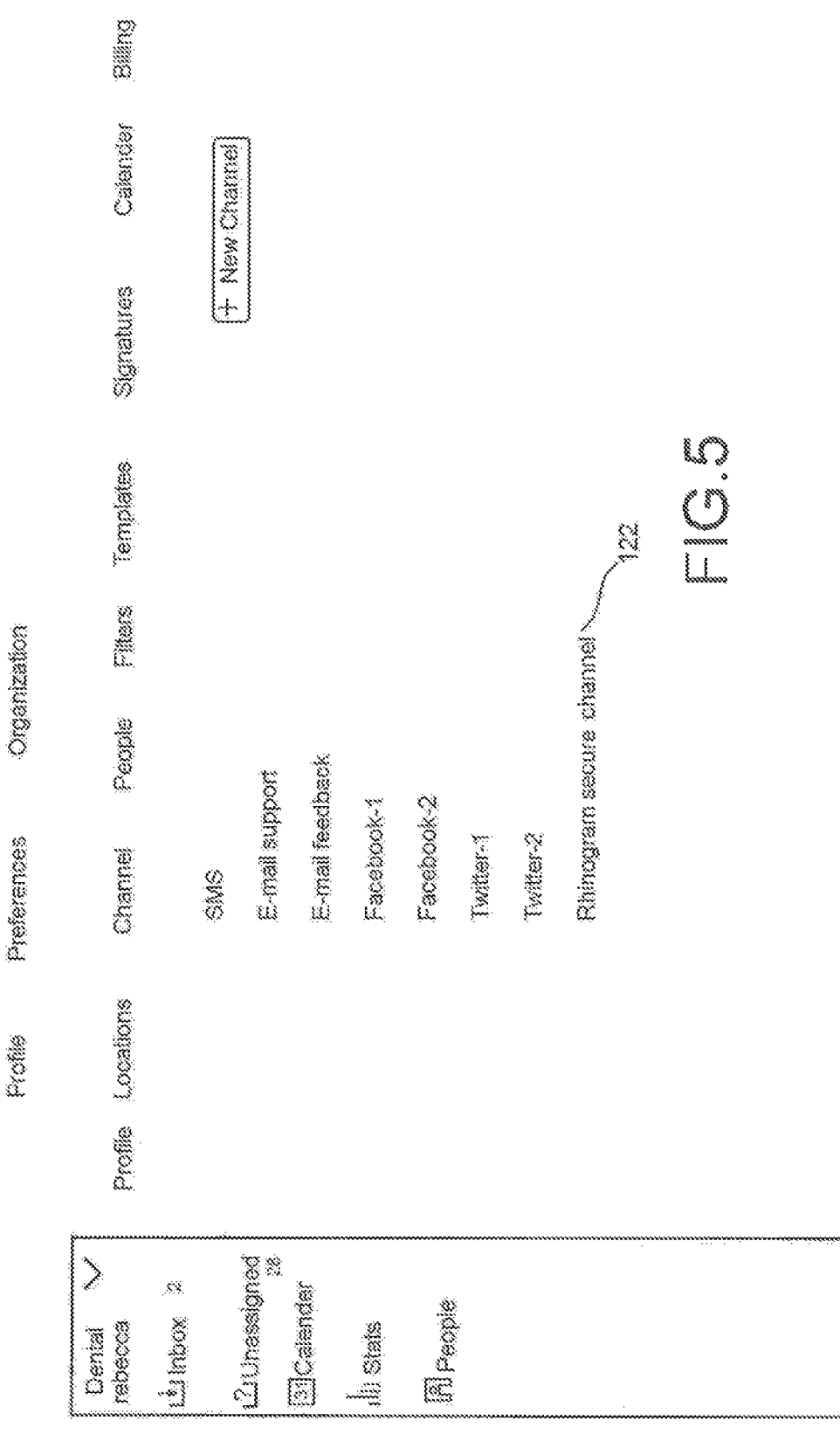
FIG. 5 is a screen shot showing channels of a first presently preferred embodiment of the present invention.

With the staff assignments such as provided by FIG. 4, it may also be possible to select various channels of communication as shown in FIG. 5 which could relate not only to teams to have the individuals or staff to which individuals communicate. The various channels of communications may be provided for not only customers but also for staff. One will note that a secure channel 122 is illustrated. Utilizing a secure channel 122, it may be that the application itself is utilized as a communication portal and may be selected as an app by the customer as well as the staff for communication there between in a secure manner which would also include security for any attachments provided. Furthermore, in the event that a customer did not have the secure channel as a communication port, it may be that if secure data information is desired to be provided to the customer that a traditional communication channel such as SMS text, e-mail or other communication could be sent to a customer with a message assigned "Click Here" to retrieve secure information such as PHI and/or other confidential information so the customer would then click on the link to then access the secure channel 122 which could be via a website or otherwise.

Figure 6:
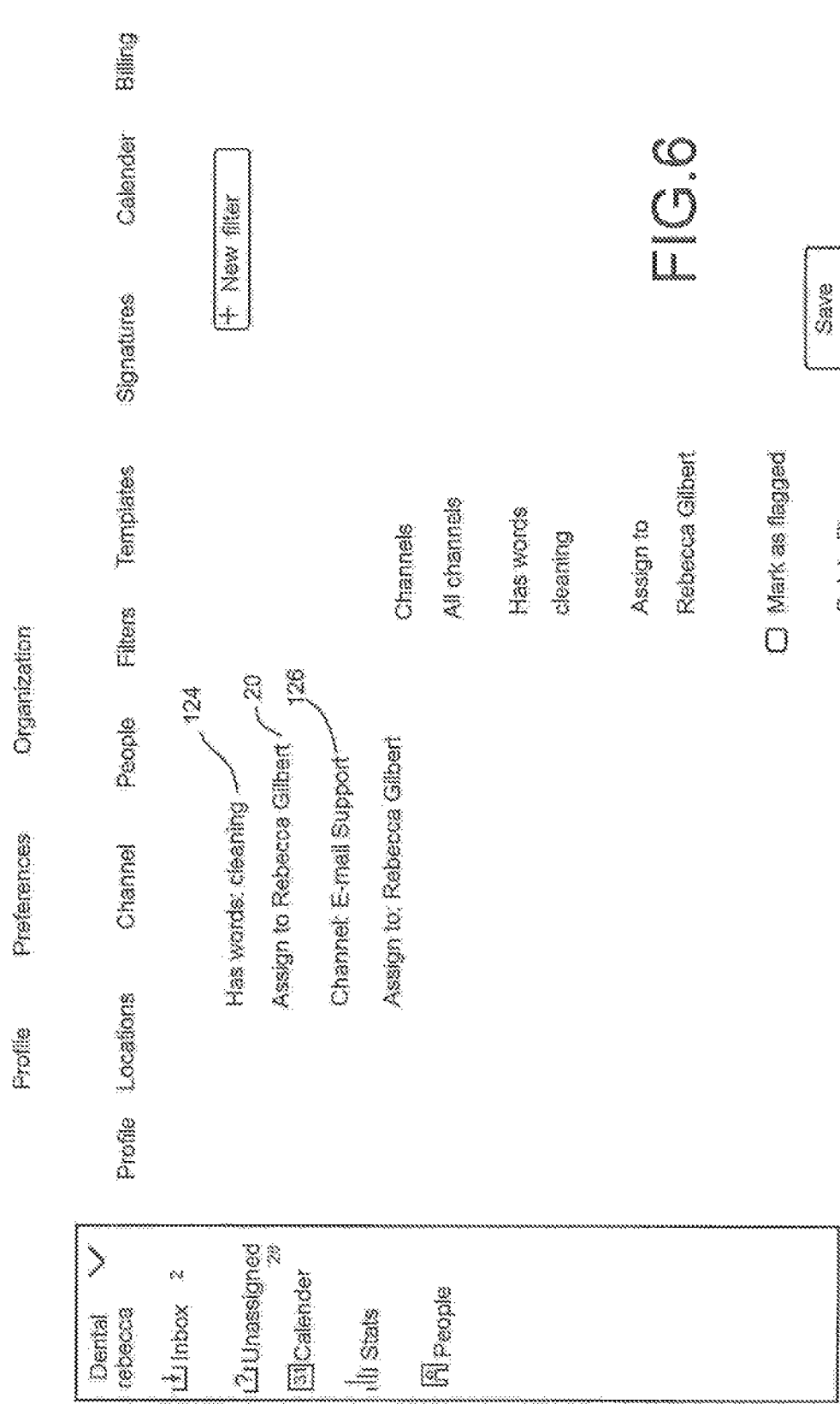
FIG. 6 is a screen shot of the presently preferred embodiment showing filters of a first presently preferred embodiment of the present invention.
Figure 8:
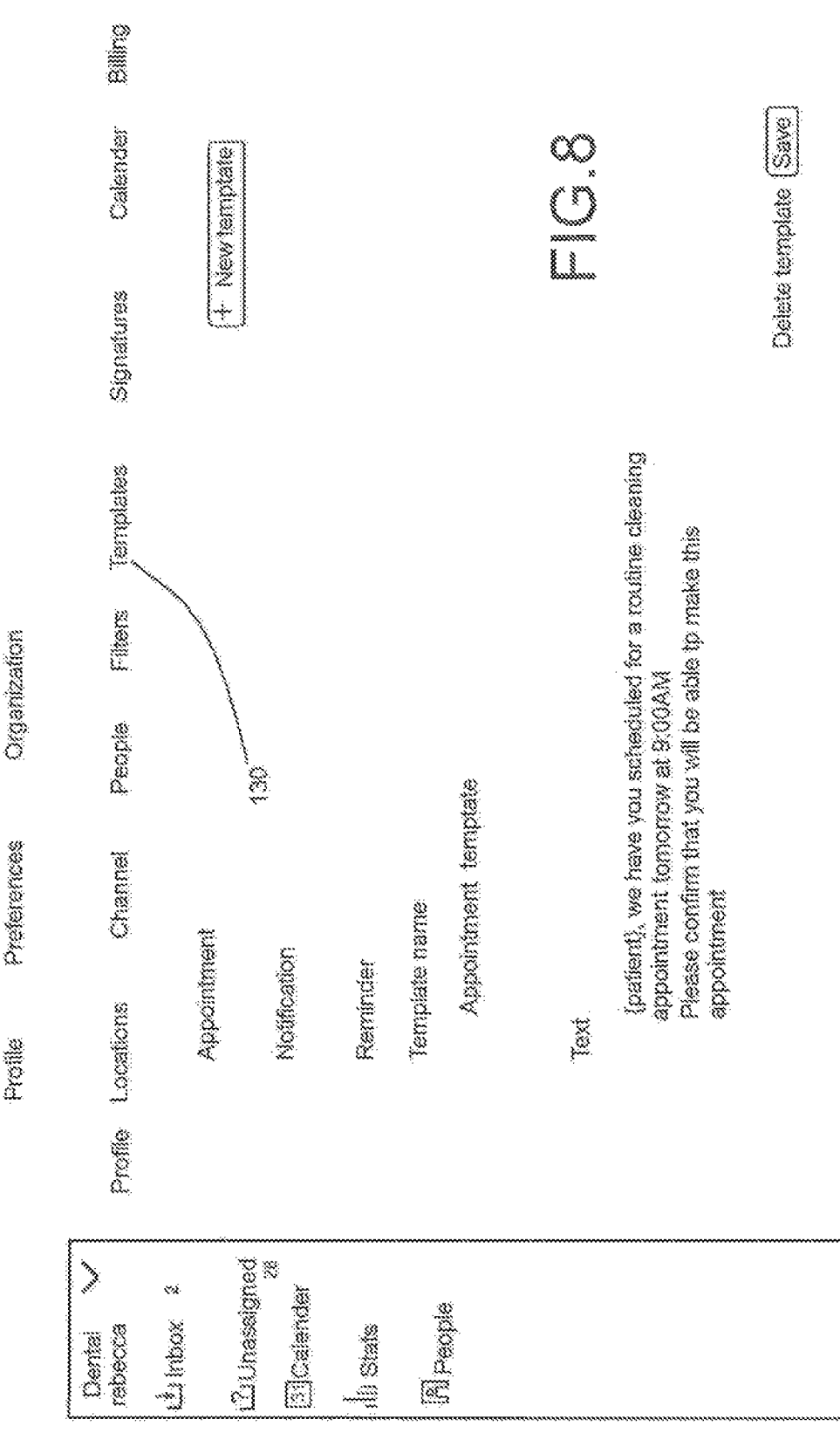
FIG. 8 is a screen shot showing templates of a first presently preferred embodiment of the present invention.

As shown in FIG. 6, it is also possible that a user, such as user 20 can select words such as filter word 124 for "cleaning" and/or a channel 126 for selection so that should any new customer contacting via e-mail may be automatically assigned to a staff member 20. Furthermore, any one requesting a cleaning 124 for a particular team may also be assigned to that particular individual for scheduling purposes. This would be particularly advantageous for those companies which have a different scheduling software, although it is anticipated that certainly this technology is applicable to coordinate with scheduling software they have on the marketplace.

FIG. 7 shows a screen shot of the selection of notifications 128 which provides various options for notifying staff members of a particular team. Templates 130 shown in FIG.

Figure 9:
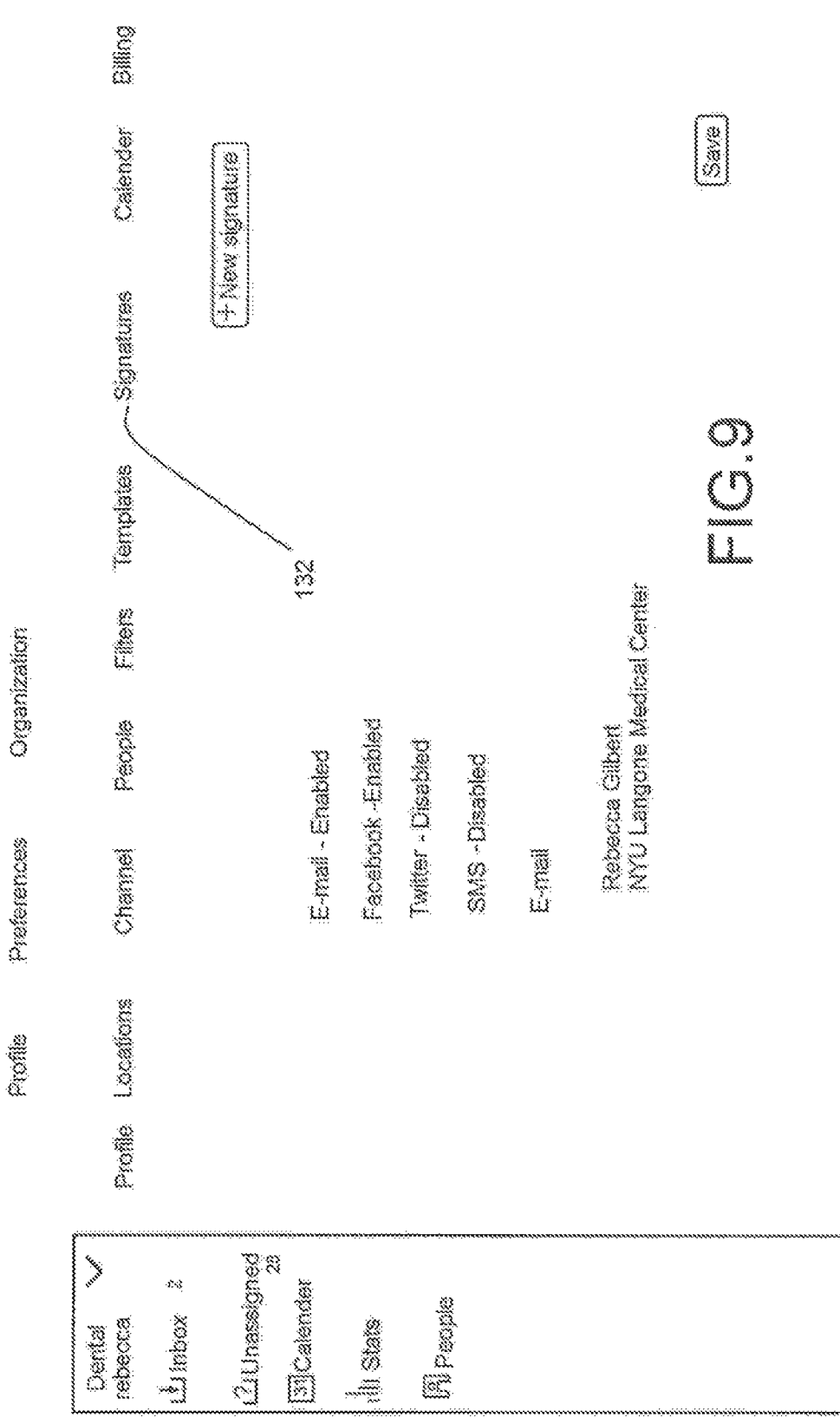
FIG. 9 is a screen shot showing signatures of a first presently preferred embodiment of the present invention.
Figure 10:
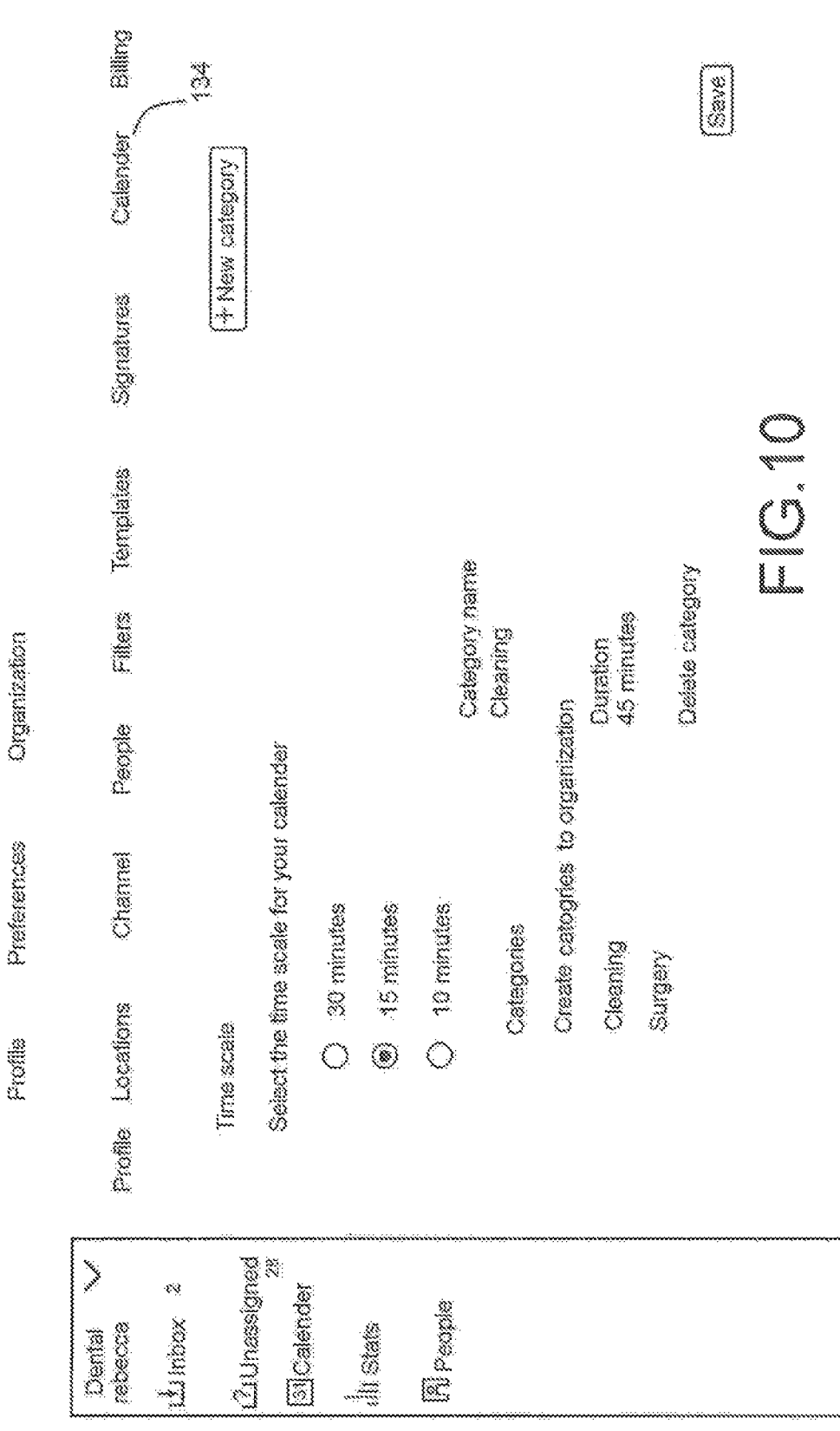
FIG. 10 is a screen shot showing calendar options of a first presently preferred embodiment of the present invention.

8 could be changed such as to provide automated templates for responding to various inquiries from customers which could search the text of the incoming communication and then provide a suggested template for at least some embodiments or otherwise be usable by the staff to simplify the response times. Signatures 132 could be provided such as shown in FIG. 9 or otherwise. Furthermore, calendar options 134 could be provided as shown in FIG. 10 or otherwise.

Figure 11:
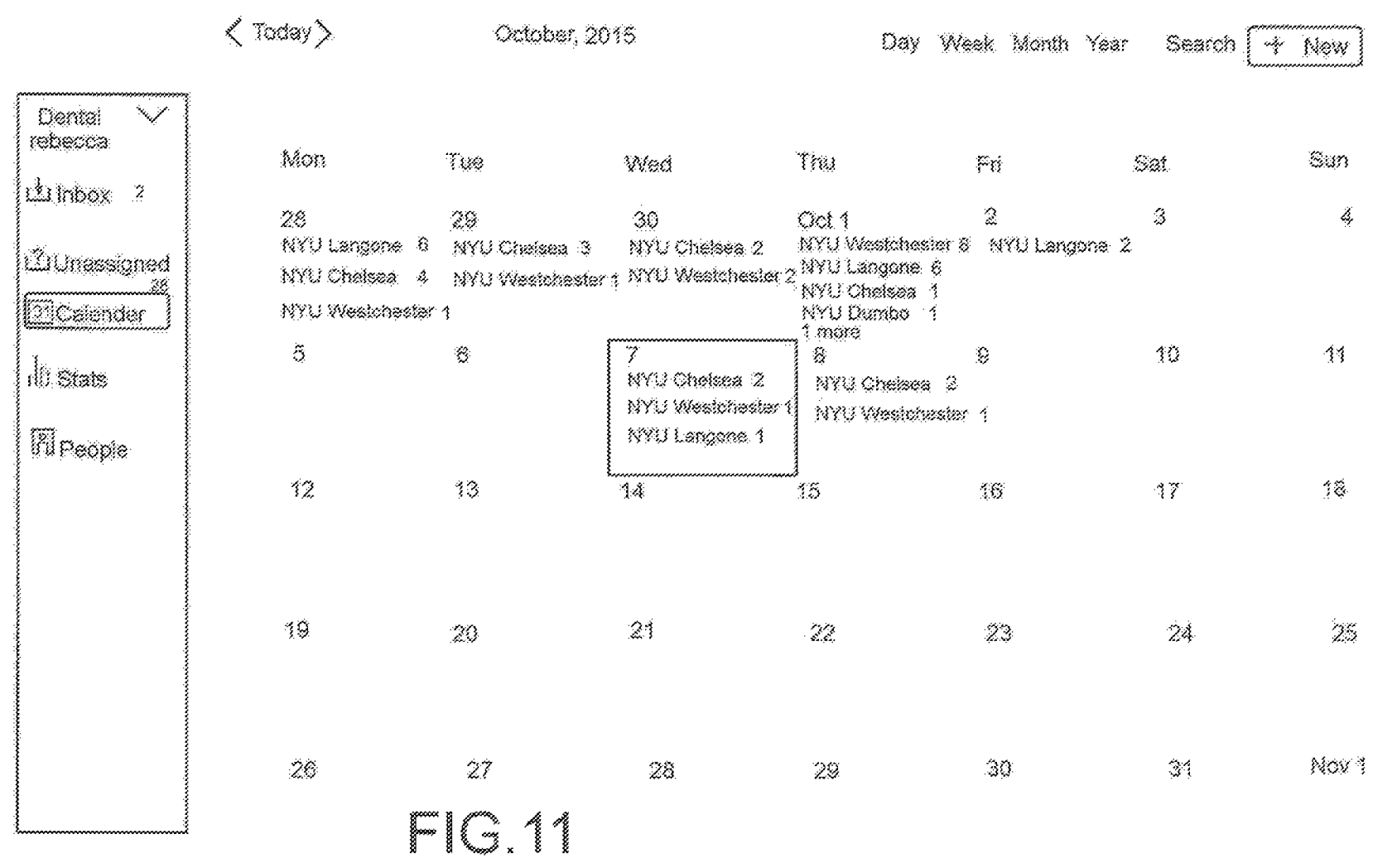
Figure 12:
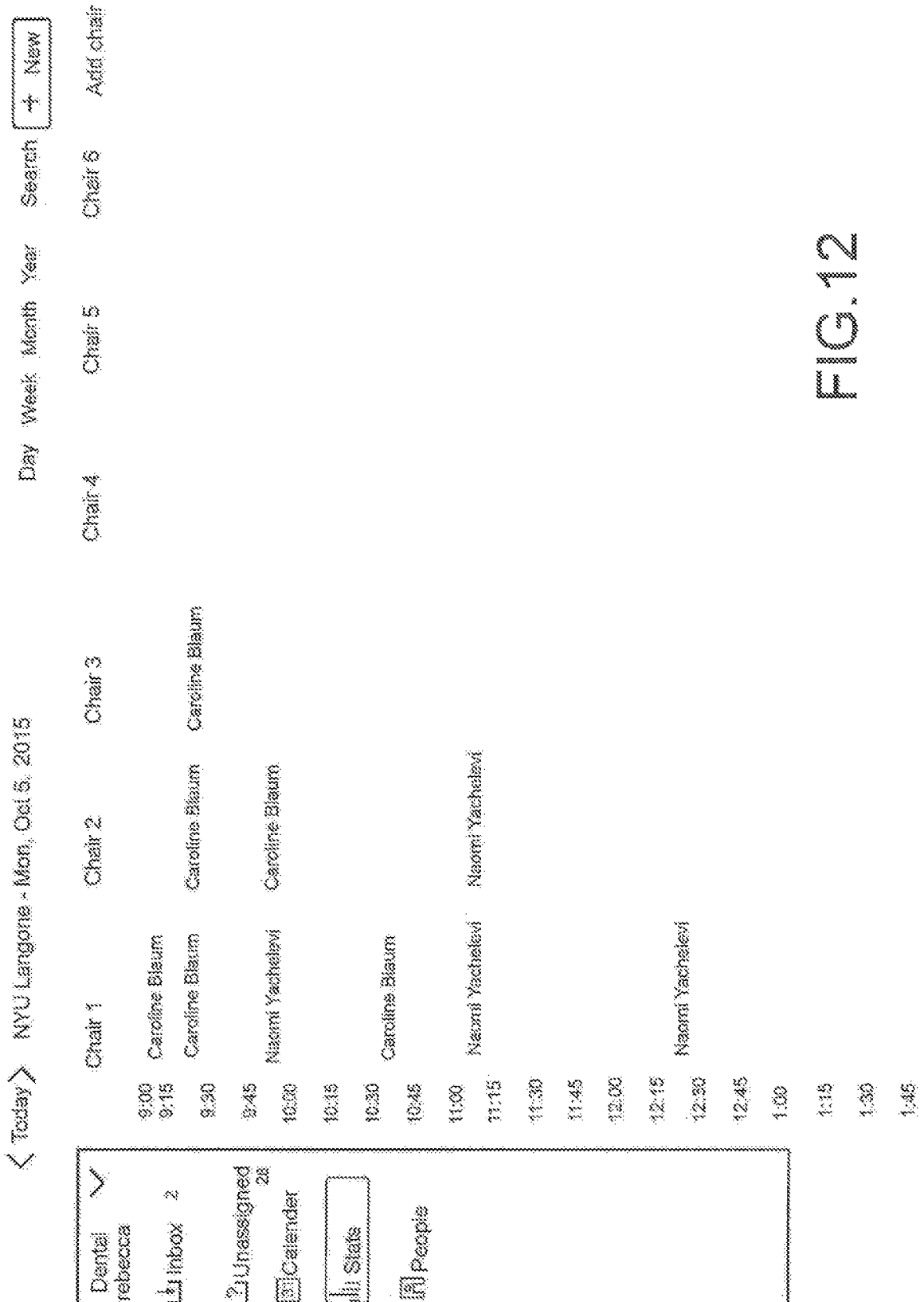
FIG. 12 is a screen shot showing second calendar of a first presently preferred embodiment of the present invention.
Figure 13:
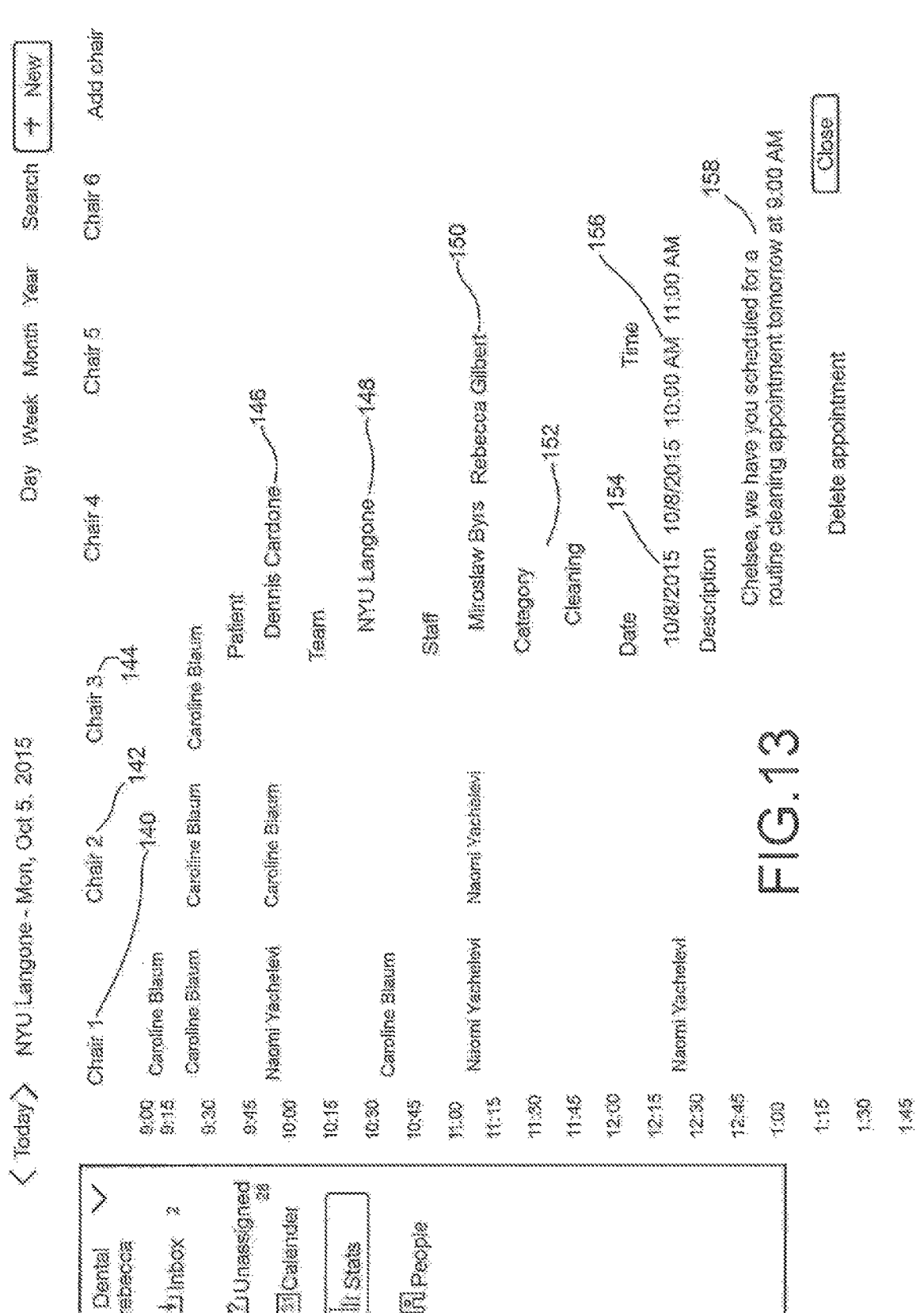
FIG. 13 is a screen shot showing a chair orientation based on the calendar view of a first presently preferred embodiment of the present invention.
Figure 14:
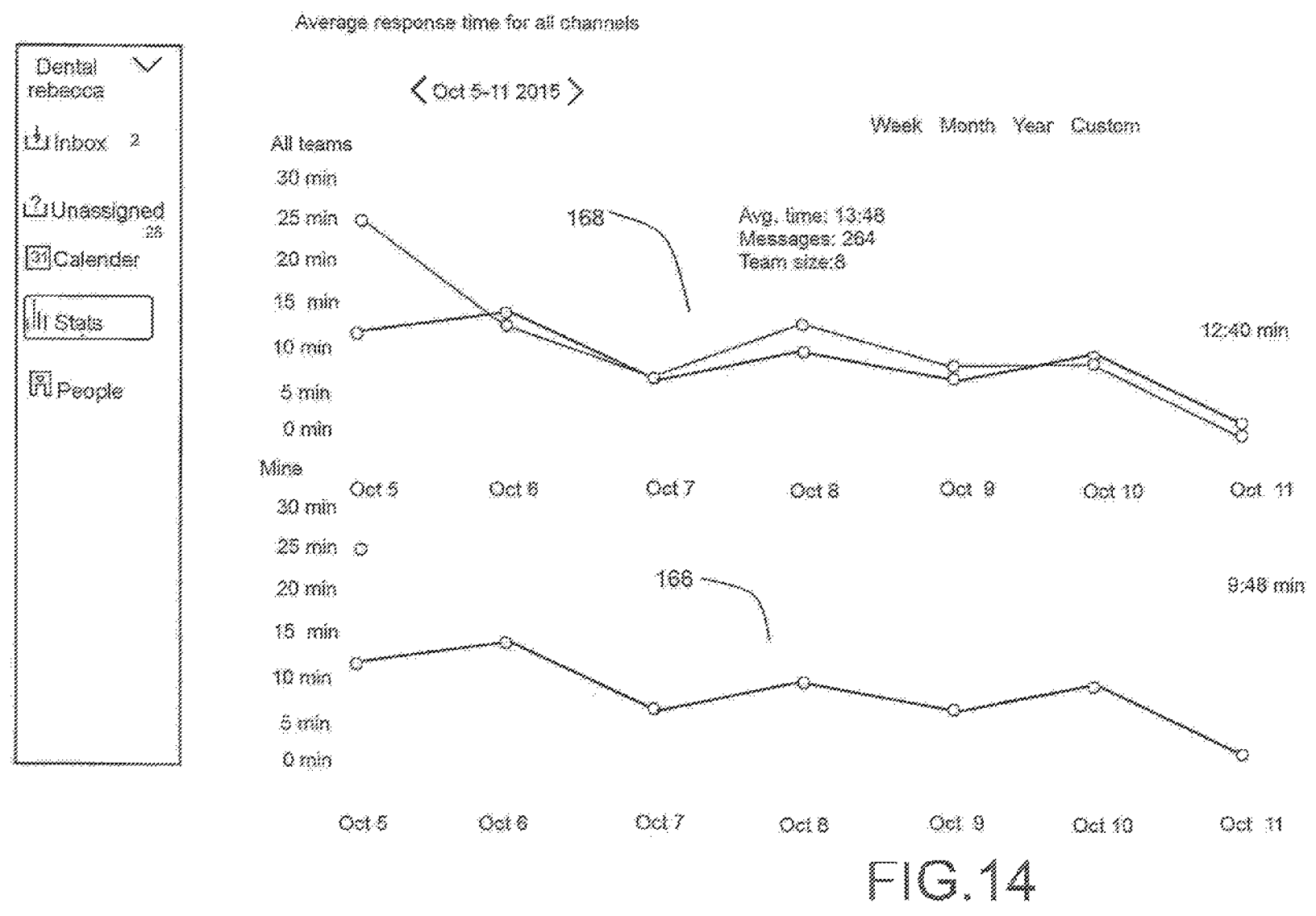

FIG. 11 shows a first calendar display showing a month display of possible appointments scheduled by various teams on various days. FIG. 12 shows a particular team scheduling. FIG. 13 shows a particular day being scheduled relative to chairs such as chairs 140,142,144, etc., possibly identifying a patient 146, team 148, a staff 150, a description of the anticipated work 152, dates and times 154,156, as well as a possible description 158. Deleting appointment may be provided at step 160 and the ability to close may be provided at step 162. FIG. 14 shows a feature and the ability to track response times of not only individuals such as at graph 166 but also of the team 168 to improve customer service.

When various users or potential customers shown in FIG. 15 interface with the company 200 having computer 10, they typically do through the various devices such as a cell phone 170 or a computer 180 which could certainly be a laptop, tablet or other computer. They then could be interfaced wirelessly through the internet, WI FI or other communications system 182 so as to reach the company 200 to software on computer 10 or run from the cloud and displayed on computer 10. Each of these customers 170,180 can be the preferred channel of communication and the integrated software system of company 200 shown on computer 10 may display as provided in FIG. 1 as each of the various communications are received. It may be that a new communication is received from an unknown individual 182 which is yet to be assigned. Communication 182 may be assigned to staff member 58 possibly automatically by the software and/or by an administrator even without knowing the identity of the potential customer 82.

Then, as described above, the communication once assigned to either principally or additionally to automatically or by an administrator or software 10 so that particular individuals may be assigned the responsibility to respond to the communication (or they may be left unassigned so that those staff members that have time may even go through unassigned communications and/or respond back to). It seems that for many embodiments the assignment of responsibility may improve the performance of the company 200. It may be that as the computer 10 receives those communications that an outflow of communications goes to staff members 12,14 on their respective channels such as their hand-held computers but preferably through the application itself (or they certainly could be sent as well or instead through SMS text, e-mail or other communications such as through WI FI 184 as well to the various devices used by the staff members. The communications from staff proceed back through the system and software sends the message to the customer preferably through their desired channel(s) of communication.

One important difference is that when communicating through this system the customers at 170,180 do not have the direct contact numbers of the staff 12,14 but instead go through the company 200 in order to reach those individuals. In this way, if the staff members were to leave to go to another company, all the communications would be retained by the company 200 as having communicated with the company 200. Additionally, if the communications provided to the staff 12,14 are through the system 10 and not through their own messaging protocols, then the staff members could be prevented from access to all the contacts and/or communications of the company 200 after leaving.

Additionally, the system, particularly when utilizing a secure communication channel of the system, allows for the secure transmission and receipt of personal health information such as by doctors' offices, dentists, orthodontists, stock brokers and/or other businesses for which sensitive material may be desired not to be provided in an unencrypted format. Many embodiments maintain communications with particular customers as a permanent communication record for those customers which is retained within the control of the company.

Accordingly, as one can see through the presently preferred embodiments of the present invention, an improved communications portal is provided for business to customer communication in which the business retains control and with the communications sent in by the customer while coordinating better customer service by the business. The communications back to the customer are provided in a way so as to be tracked by the company for both promptness and accountability. Additionally, communications with the customers can be done in a secure manner so as to be able to provide secure information back and forth even if the customers do not have an app for secure communications provided on their computing devices 170,180. This way the company 200 can comply with HIPAA and/or other regulations requiring the protection of secure information.

Figure 19:
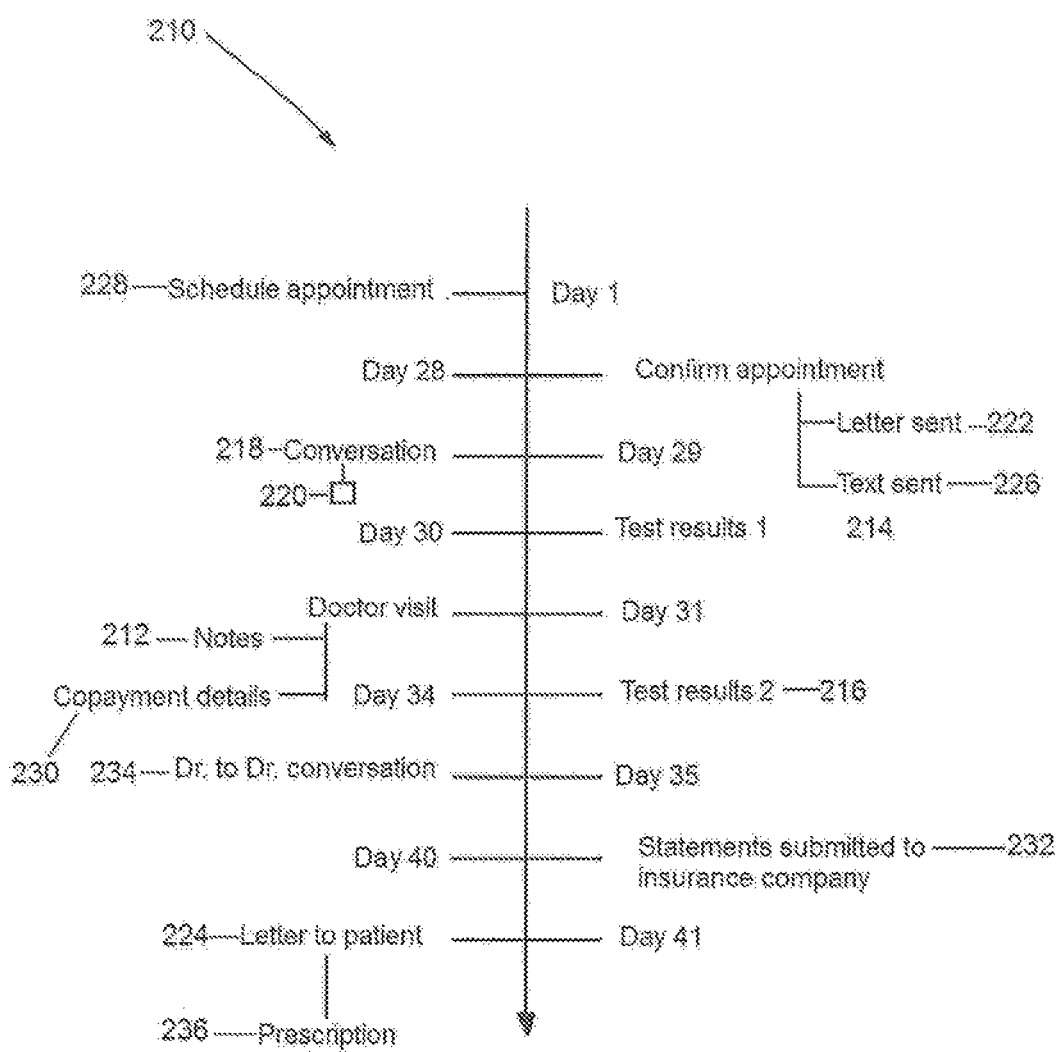
FIG. 19 is a screen shot showing a time line feature for at least some embodiments of the present invention.

FIG. 19 shows a display 210 as could be provided on computer 300, or even any of 302,304,310,312 or others as desired by the company, showing a time-line view of the record, such as an Electronic Health Record (EHR) of an existing customer. Not only are medical information such as notes 212 from a doctor or test results 214 and/or 216 recorded in chronological order, but also communications received from or with the customer 218 or patient as appropriate depending on the business of the company possibly including submission of a form 220 such as an agreement for services and/or other documents. Outgoing communications such as letters 222 and/or 224, texts 226, or even appointment scheduling 228 which might be an automated e-mail or other scheduling method. Payment information (accounting records 230,232) could be provided, doctor to doctor communications 234, prescriptions 236 which might be provided to a patient and/or directly to a pharmacy, and/or other conversation or non-conversation events. Other businesses may have notes regarding services and/or products provided, such as an electrical contractor providing services for a company, purchase requests and confirmations such as a stock broker, and/or other entries to be displayed.

Figure 20:
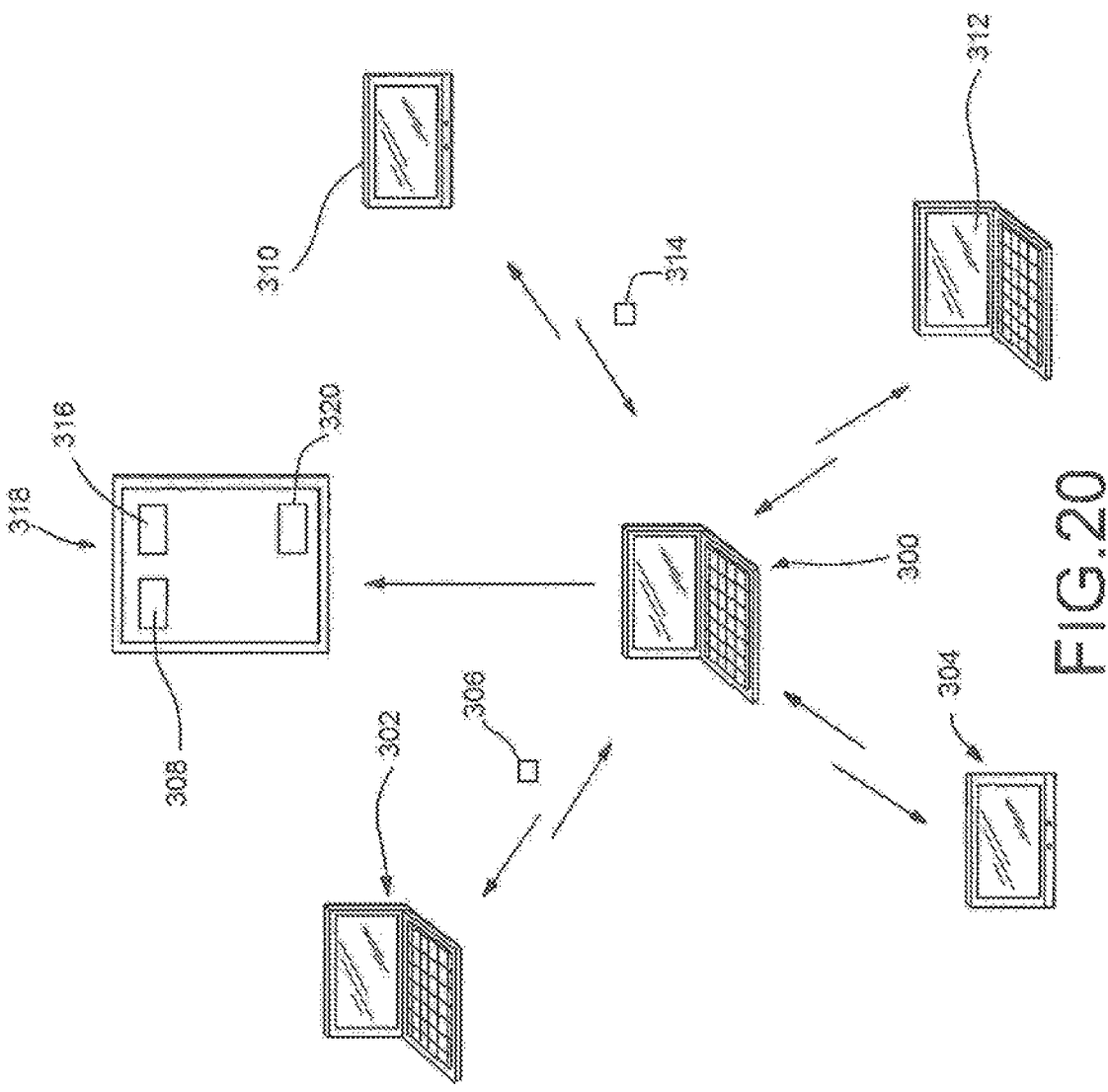
FIG. 20 is a schematic diagram showing communication paths contemplated by many embodiments of the present invention.
Figure 21:
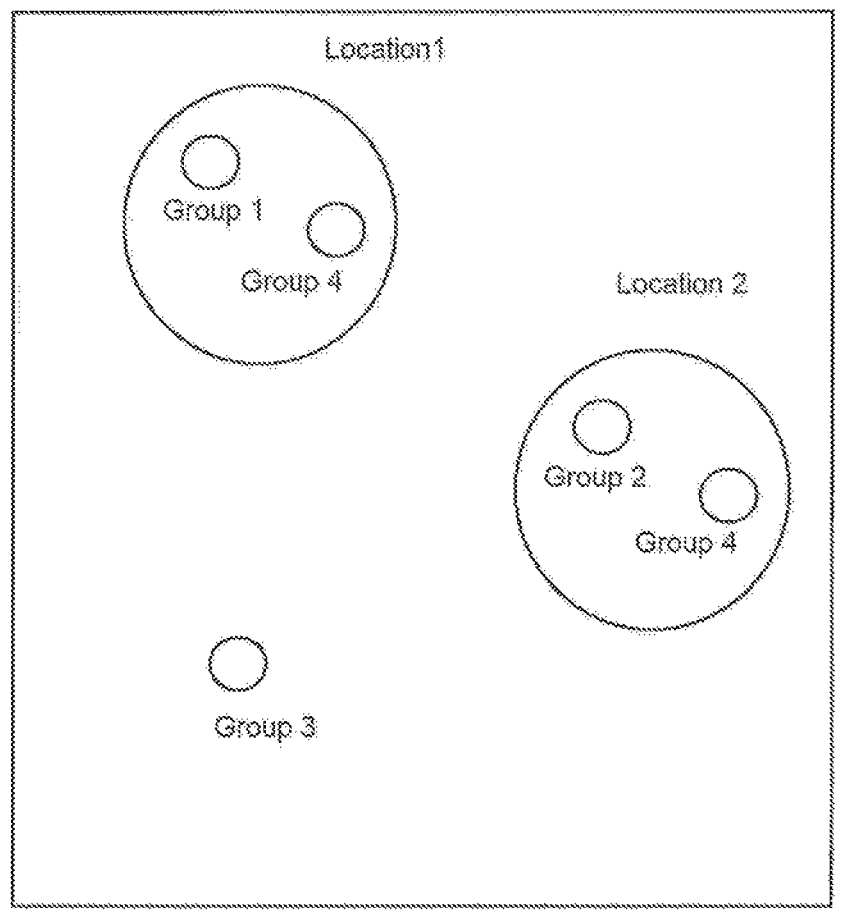
FIG. 21 is a schematic diagram showing possible communication situations of the present invention.

A method of using a multi-format communications system can comprise a remote communications device as shown in FIG. 20, such as but not limited to a computer 302 or a phone 304, such as possibly a smart phone as illustrated of an existing or a potential customer of a company sending a communication in a first format, such as but not limited to one of email, SMS text, voice, or even video, such as over internet protocol, Facebook, twitter, fax, and a secure channel to a company computer 300 which could be a server or any other computer provided for or maintained by the company. The computer 300 receives the communication from the communications device 302,304 from the existing or potential customer and records a time stamped first entry 308 of the existing customer.

The computer 300 then sends the communication to one of an individual and team of individuals (i.e., two or more, such as to phone 310 or computer 312 shown) of the company for response to the existing customer through a private channel controlled by the company which could be through an app (application), website or other controlled channel, whereby the individual has access only through being associated with (or granted by) the company, and the company information is only accessible to the individual through the portal provided by the company to and through the phone 310 or computer 312 of the individual.

The individual whether a member of the team (if so a member) then responds back to the existing or potential customer from their phone or computer 312 with a response 314 recorded as time stamped second entry 316 with the response sent through the computer 300 to be delivered to the potential or existing customer preferably in the first format (but possibly through other formats) whereby the computer 300 provides a permanent record relative to the existing customer of the first and second entries 308,316 as a portion of a file 318 for the existing customer as could be represented in FIG. 19 and elsewhere, whereby the file 318 further comprises personal confidential information of the existing customer related to one of the health of the customer and the financial business of the customer performed for the customer by the company.

Figure 22:
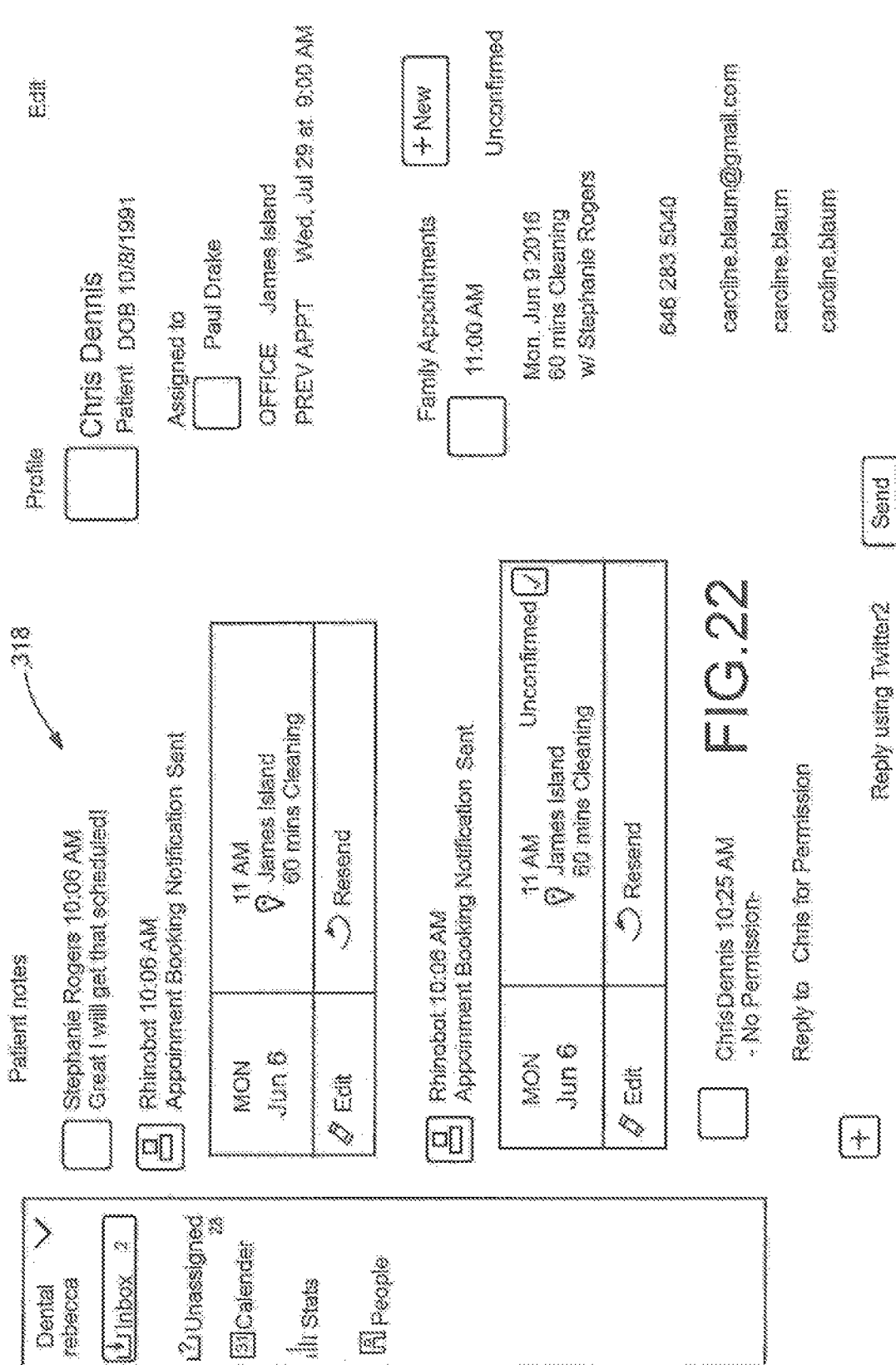
FIG. 22 is a screen shot showing a timeline arrangement for at least some of embodiments of the present invention.

The file 318 can display in a timeline format such as shown in FIG. 22 whereby each entry can be timestamped when entered into the file including communications from the existing customer, and each entry can be displayed in chronological order, including personal information (possibly, if not likely confidential information 320, such as but not limited to financial information such as stocks or other investment vehicles and/or cash from a portfolio, PHI, EHR information and/or other information). At least portions of the file 318 can communicate with practice management software (PMS) for scheduling or other purposes. Still other portions could communicate with accounting software or other software for various purposes.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method for managing communications between remote user devices accessing a plurality of different communication channels, a computer system of an organization, and a plurality of team member devices, the method comprising:

receiving, at the computer system via a first communication channel of the plurality of different communication channels, a first communication from a remote user device, wherein the first communication comprises first information associated with a remote user;

receiving, at the computer system via a second communication channel, a second communication from a team member device, wherein the second communication comprises second information associated with the remote user, wherein the second communication channel is a private communication channel controlled by the organization over which the team member device securely transmits the second communication to the computer system, and wherein the second communication channel is different than the first communication channel;

generating, at the computer system, a third communication to send to the remote user device via the first communication channel, wherein the third communication comprises third information associated with the remote user and further comprises a user-actionable element associated with at least one of a secure application, secure channel, or secure website, and wherein the computer system is configured to communicate confidential information associated with the remote user via the at least one secure application, secure channel, or secure website to the remote user device if the remote user activates the user-actionable element in the third communication;

accessing, by first software and second software on the computer system, a file associated with the remote user on the computer system, wherein the file contains each of the first, second, and third information that the computer system transmits or receives over the different first and second communication channels, and wherein a first portion of the file is communicated to the first software and a second portion of the file is communicated to the second software for different purposes; and using, by the computer system, the file to create a graphical display depicting at least a portion of the contents of each of the first, second, and third information in a chronological order in a timeline format.

2. The method of claim 1, further comprising:

associating, by the computer system, a respective timestamp with each of the first, second, and third information;

storing, by the computer system, each of the first, second, and third information together with their respective timestamps as different entries in the file associated with the remote user; and creating, by the computer system, the graphical display depicting at least a portion of the contents of each of the first, second, and third information in the chronological order in the timeline format based on the timestamps respectively associated with the first, second, and third information in the file.

3. The method of claim 1, further comprising displaying, by the computer system, a user interface including options for selecting multiple different views, wherein one of the options corresponds to a view comprising the graphical display depicting at least a portion of the contents of each of the first, second, and third information in the chronological order in the timeline format.

4. The method of claim 1, wherein the second communication channel is a private channel controlled by the organization.

5. The method of claim 1, wherein the organization is a health care provider and the remote user is a patient.

6. The method of claim 5, wherein at least one of the first, second, and third information comprises personal health information of the patient.

7. The method of claim 6, wherein the personal health information comprises medical test results of the patient.

8. The method of claim 6, wherein the personal health information comprises doctor notes associated with the patient.

9. The method of claim 1, wherein at least one of the first, second, and third information comprises financial information of the remote user.

10. A communication system for communicating with remote user devices accessing a plurality of different communication channels and a plurality of team member devices associated with an organization, the communication system comprising:

a communication interface configured to receive:

a first communication from a remote user device via a first communication channel, wherein the first communication comprises first information associated with a remote user, and a second communication from a team member device via a second communication channel, wherein the second communication comprises second information associated with the remote user, wherein the second communication channel is a private communication channel controlled by the organization over which the team member device securely transmits the second communication to the communication system, and wherein the second communication channel is different than the first communication channel;

at least one processor configured to generate a third communication to send to the remote user device via the first communication channel, wherein the third communication further comprises third information associated with the remote user and further comprises a user-actionable element associated with at least one of a secure application, secure channel, or secure website, wherein the communication system is configured to communicate confidential information associated with the remote user via the at least one secure application, secure channel, or secure website to the remote user device if the remote user activates the user-actionable element in the third communication;

a memory configured to store a file associated with the remote user, wherein the file is configured to store entries corresponding to each of the first, second, and third information associated with the remote user; and wherein the at least one processor is further configured to:

access, using first software and second software, the file associated with the remote user, wherein a first portion of the file is communicated to the first software and a second portion of the file is communicated to the second software for different purposes; and use the file to create a graphical display to depict at least a portion of the contents of each of the first, second, and third information in a chronological order in a timeline format.

11. The system of claim 10, wherein a respective timestamp is associated with each of the first, second, and third information, and wherein the file is further configured to store each of the first, second, and third information together with their respective timestamps as different entries.

12. The system of claim 10, wherein the at least one processor is further configured to create a user interface including options for selecting multiple different views, wherein one of the options corresponds to a view comprising the graphical display depicting at least a portion of the contents of each of the first, second, and third information in the chronological order in the timeline format.

13. The system of claim 10, wherein the organization is a health care provider and the remote user is a patient, and wherein at least one of the first, second, and third information comprises personal health information of the patient.

14. A method for managing communications between a patient and a health care provider having a plurality of team members including at least one doctor and a computer system configured to communicate with the patient's device and the doctor's device, the method comprising:

receiving, at the computer system, a first communication from the patient's device via a first communication channel of a plurality of different communication channels available to the patient, wherein the first communication comprises first information associated with the patient;

receiving, at the computer system, a second communication from the doctor's device via a second communication channel, wherein the second communication comprises second information associated with the patient, and wherein the second communication channel is different than the first communication channel;

generating, at the computer system, a third communication to send to the patient's device via the first communication channel, wherein the third communication comprises third information associated with the patient and further comprises a user-actionable element associated with at least one of a secure application, secure channel, or secure website, wherein the computer system is configured to communicate personal health information associated with the patient via the at least one of a secure application, secure channel, or secure website to the patient's device if the patient activates the user-actionable element in the third communication;

accessing, by first software and second software on the computer system, a file associated with the patient on the computer system, wherein the file contains each of the first, second, and third information that the computer system transmits or receives over the different first and second communication channels, and wherein a first portion of the file is communicated to the first software and a second portion of the file is communicated to the second software for different purposes; and using, by the computer system, the file to create a graphical display depicting at least a portion of the contents of each of the first, second, and third information in a chronological order in a timeline format.

15. The method of claim 14, wherein the first information comprises payment information associated with the patient.

16. The method of claim 14, wherein the second information comprises at least one of test results or doctor's notes associated with the patient.

17. The method of claim 14, wherein the third information comprises appointment scheduling information associated with the patient.

18. The method of claim 14, wherein the first communication comprises a text message received from the patient.

19. The method of claim 14, wherein the file is an electronic health record associated with the patient.

20. The method of claim 14, wherein the doctor is a dentist.

21. The method of claim 1, wherein the user-actionable element in the third communication is a link that can be clicked by the remote user.

22. The system of claim 10, wherein the user-actionable element in the third communication is a link that can be clicked by the remote user.

23. The method of claim 14, wherein the user-actionable element in the third communication is a link that can be clicked by the remote user.

* * * * *